(12) United States Patent
Takeda et al.

(10) Patent No.: US 9,522,244 B2
(45) Date of Patent: Dec. 20, 2016

(54) BRAIN COOLING APPARATUS AND BRAIN COOLING DEVICE SUITABLE THERETO

(75) Inventors: Yoshimasa Takeda, Okayama (JP); Kiyoshi Morita, Okayama (JP); Hiroshi Hashimoto, Izumi (JP); Hidekazu Tsuji, Izumi (JP); Masatomo Kokubu, Izumi (JP)

(73) Assignees: KAIKEN IKI KABUSHIKI KAISHA, Osaka-shi, Osaka (JP); NATIONAL UNIVERSITY CORPORATION OKAYAMA UNIVERSITY, Okayama-shi, Okayama (JP)

( * ) Notice: Subject to any disclaimer, the term of this patent is extended or adjusted under 35 U.S.C. 154(b) by 1026 days.

(21) Appl. No.: 13/580,394

(22) PCT Filed: Feb. 21, 2011

(86) PCT No.: PCT/JP2011/000947
§ 371 (c)(1),
(2), (4) Date: Aug. 22, 2012

(87) PCT Pub. No.: WO2011/102146
PCT Pub. Date: Aug. 25, 2011

(65) Prior Publication Data
US 2012/0323296 A1 Dec. 20, 2012

(30) Foreign Application Priority Data
Feb. 22, 2010 (JP) .................................. 2010-036374

(51) Int. Cl.
*A61F 7/12* (2006.01)
*A61M 16/04* (2006.01)
(Continued)

(52) U.S. Cl.
CPC ............ *A61M 16/04* (2013.01); *A61F 7/0085* (2013.01); *A61F 7/10* (2013.01); *A61F 7/123* (2013.01);
(Continued)

(58) Field of Classification Search
CPC ............................. A61F 7/12; A61F 2007/126
(Continued)

(56) References Cited

U.S. PATENT DOCUMENTS 6,149,624 A * 11/2000 McShane .................. A61F 7/12
604/113
7,189,253 B2 3/2007 Lunderqvist et al.
(Continued)

FOREIGN PATENT DOCUMENTS

| JP | 2005-287548 | 10/2005 |
|---|---|---|
| JP | 2007-75505 | 3/2007 |

(Continued)

*Primary Examiner* — Jocelyn D Ram
(74) *Attorney, Agent, or Firm* — Gerald E. Hespos; Michael J. Porco; Matthew T. Hespos

(57) ABSTRACT

A brain cooling apparatus is provided that can circulate a fluid between a containing unit of a brain cooling device and the brain cooling apparatus while maintaining an appropriate pressure of the fluid in the containing unit, and a brain cooling device suitable thereto also is provided. A control device circulates a physiological saline solution between a storage tank and a cuff by driving a first pump in a direction in which the physiological saline solution flows toward the cuff, and driving a second pump in a direction in which the physiological saline solution flows toward the storage tank. In this state, the control device adjusts the rotation speed of at least the second pump, so that the pressure of the physiological saline solution in the cuff becomes a preset target pressure.

12 Claims, 20 Drawing Sheets

(51) Int. Cl.
*A61F 7/10* (2006.01)
*A61M 19/00* (2006.01)
*A61F 7/00* (2006.01)

(52) U.S. Cl.
CPC ..... *A61M 16/0409* (2014.02); *A61M 16/0438* (2014.02); *A61M 19/00* (2013.01); *A61B 2090/065* (2016.02); *A61F 2007/0002* (2013.01); *A61F 2007/0056* (2013.01); *A61F 2007/0092* (2013.01); *A61M 16/0434* (2013.01); *A61M 2205/3606* (2013.01)

(58) Field of Classification Search
USPC .................................................. 607/104, 105
See application file for complete search history.

(56) References Cited

U.S. PATENT DOCUMENTS

| | | |
|---|---|---|
| 8,221,481 B2 | 7/2012 | Takeda et al. |
| 2004/0210281 A1 | 10/2004 | Dzeng et al. |
| 2005/0096714 A1* | 5/2005 | Freedman, Jr. ........... A61F 7/00 607/104 |
| 2005/0209662 A1 | 9/2005 | Lunderqvist et al. |
| 2005/0222652 A1 | 10/2005 | Mori |
| 2006/0161107 A1* | 7/2006 | Mantle ...................... A61F 7/12 604/113 |
| 2008/0086186 A1* | 4/2008 | Takeda ...................... A61F 7/12 607/105 |
| 2008/0275535 A1 | 11/2008 | Mori |
| 2009/0177258 A1* | 7/2009 | Takeda ................... A61F 7/123 607/105 |
| 2009/0234325 A1 | 9/2009 | Rozenberg et al. |
| 2010/0204765 A1* | 8/2010 | Hall ......................... A61F 7/12 607/105 |
| 2010/0324635 A1* | 12/2010 | Kreck ...................... A61F 7/12 607/105 |
| 2011/0046547 A1 | 2/2011 | Mantle |
| 2013/0030411 A1* | 1/2013 | Kreck ...................... A61F 7/12 604/514 |
| 2013/0190744 A1* | 7/2013 | Avram ..................... A61F 7/10 606/21 |

FOREIGN PATENT DOCUMENTS

| | | |
|---|---|---|
| JP | 2007-529267 | 10/2007 |
| WO | 03/105736 | 12/2003 |

* cited by examiner

BRAIN COOLING APPARATUS AND BRAIN COOLING DEVICE SUITABLE THERETO

BACKGROUND OF THE INVENTION

Field of the Invention

The present invention relates to a device for cooling a brain of a living body.

Description of the Background Art

If a living body, including a human body, enters a state where the respiratory functions and the circulatory functions are incompetent, such as cardiac arrest (hereafter "cardiac arrest state"), oxygen supply to the brain becomes insufficient. It is known that this lack of oxygen supply destroys brain cells, that is, causes ischemic neuronal damage.

Artificial respiration and other cardiac resuscitation treatments can be performed on a living body in the cardiac arrest state. However even if the living body is resuscitated from the cardiac arrest state by these treatments, a mentioned ischemic neuronal damage may give a sequela to the brain.

With the foregoing in view, recently a so called "hypothermic therapy" is proposed as a treatment for preventing the ischemic neuronal damage from being caused. In hypothermic therapy, the brain is cooled by lowering the body temperature of the living body in the cardiac arrest state.

As an example of a device for performing hypothermic therapy, a brain cooling device disclosed in Japanese Patent Application Laid-Open No. 2007-75505 is known. This cooling device has a cuff which can be disposed in an esophagus of the living body by oral or transnasal insertion, a tube connected to the cuff, and a port connected to the tube on the opposite side of the cuff. The cuff is expanded by injecting cooled fluid into the cuff via the tube in a state where the cuff is disposed in the esophagus of the living body. Thereby the cuff closely contacts the inner wall of the esophagus. As a result, the blood in the blood vessels (carotid arteries) that are located near the inner wall of the esophagus and supply blood to the brain is cooled down, and therefore the brain is cooled down.

The cooling device according to Japanese Patent Application Laid-Open No. 2007-75505 has a tube for supplying the cooled fluid to the cuff (hereafter called "supply tube"), and a tube for draining the fluid from the cuff (hereafter called "drain tube") individually.

In the case of cooling the brain using the cooling device of Japanese Patent Application Laid-Open No. 2007-75505, it is preferable to circulate the fluid as follows, in terms of increasing heat exchange efficiency. That is, the cooled fluid is supplied into the cuff via the supply tube which is guided to the outside of the living body, and the fluid drained from the cuff via the drain tube which is guided to the outside of the living body, is cooled down, and the fluid is circulated back to the cuff again.

In the case of the cooling device of Japanese Patent Application Laid-Open No. 2007-75505, the cuff must be closely contacted with the esophagus of the living body to cool down the brain, but if this close contact is too vigorous and the pressure of the fluid in the cuff becomes too high, burden on the inner wall of the esophagus and on the cuff itself increases. Hence the fluid in the cuff must be maintained at an appropriate level. However holding the pressure of the fluid in the cuff at an appropriate level is not easy, since this circulation is manually performed by a medical staff.

SUMMARY OF THE INVENTION

It is an object of the present invention to provide a brain cooling apparatus that can circulate a fluid between a containing unit of a brain cooling device and the brain cooling apparatus while maintaining an appropriate pressure of the fluid in the containing unit, and a brain cooling device suitable thereto.

To solve this problem, the present invention provides a brain cooling apparatus for supplying a fluid to a containing unit of a brain cooling device and discharging the fluid from the containing unit of the brain cooling device, which has the containing unit that can be expanded by the fluid injected therein and closely contact at least a part of an area from an oral cavity to a stomach of a living body, an injection unit that can inject fluid from outside the body into the containing unit, and an ejection unit that can eject the fluid inside the containing unit to outside the body, comprising: an injection side connection unit that can be connected with the injection unit; an ejection side connection unit that can be connected with the ejection unit; a storage unit that stores the fluid; a supply channel that connects the storage unit and the injection side connection unit; a collection channel that connects the storage unit and the ejection side connection unit; a first pump that is disposed on the supply channel to flow the fluid along the supply channel; a second pump that is disposed on the collection channel to flow the fluid along the collection channel; and a control unit that controls the driving of the first pump and the second pump, wherein the control unit adjusts a driving speed of at least the second pump out of the two pumps, so that a pressure in the containing unit becomes a preset target pressure in a state of circulating the fluid between the storage unit and the containing unit by driving the first pump such that the fluid flows in a direction from the storage unit to the containing unit, and by driving the second pump such that the fluid flows in a direction from the containing unit to the storage unit.

The present invention also provides a brain cooling device that is used by being connected to the brain cooling apparatus, comprising: a containing unit that can be expanded by the fluid injected therein and closely contact at least a part of an area from an oral cavity to a stomach of a living body, in a state of being inserted orally or transnasally into a living body; an injection unit that can inject fluid from outside the body into the containing unit and can be connected to the injection side connection unit of the brain cooling apparatus; an ejection unit that can eject the fluid inside the containing unit to outside the body, and can be connected to the ejection side connection unit of the brain cooling apparatus; and a detection unit that can detect pressure of the fluid inside the injection unit or the ejection unit, and can output the detection result to the control unit of the brain cooling apparatus.

The present invention can provide a brain cooling apparatus that can circulate a fluid between the containing unit of a brain cooling device and the brain cooling apparatus while maintaining an appropriate pressure of the fluid in the containing unit, and a brain cooling device suitable thereto.

DETAILED DESCRIPTION OF THE PREFERRED EMBODIMENTS OF THE INVENTION

Embodiments of the present invention will now be described with reference to the accompanying drawings. The following embodiments are examples of carrying out the present invention, and not for limiting the technical scope of the present invention.

A preferred embodiment of the present invention will now be described with reference to the drawings.

Figure 1:
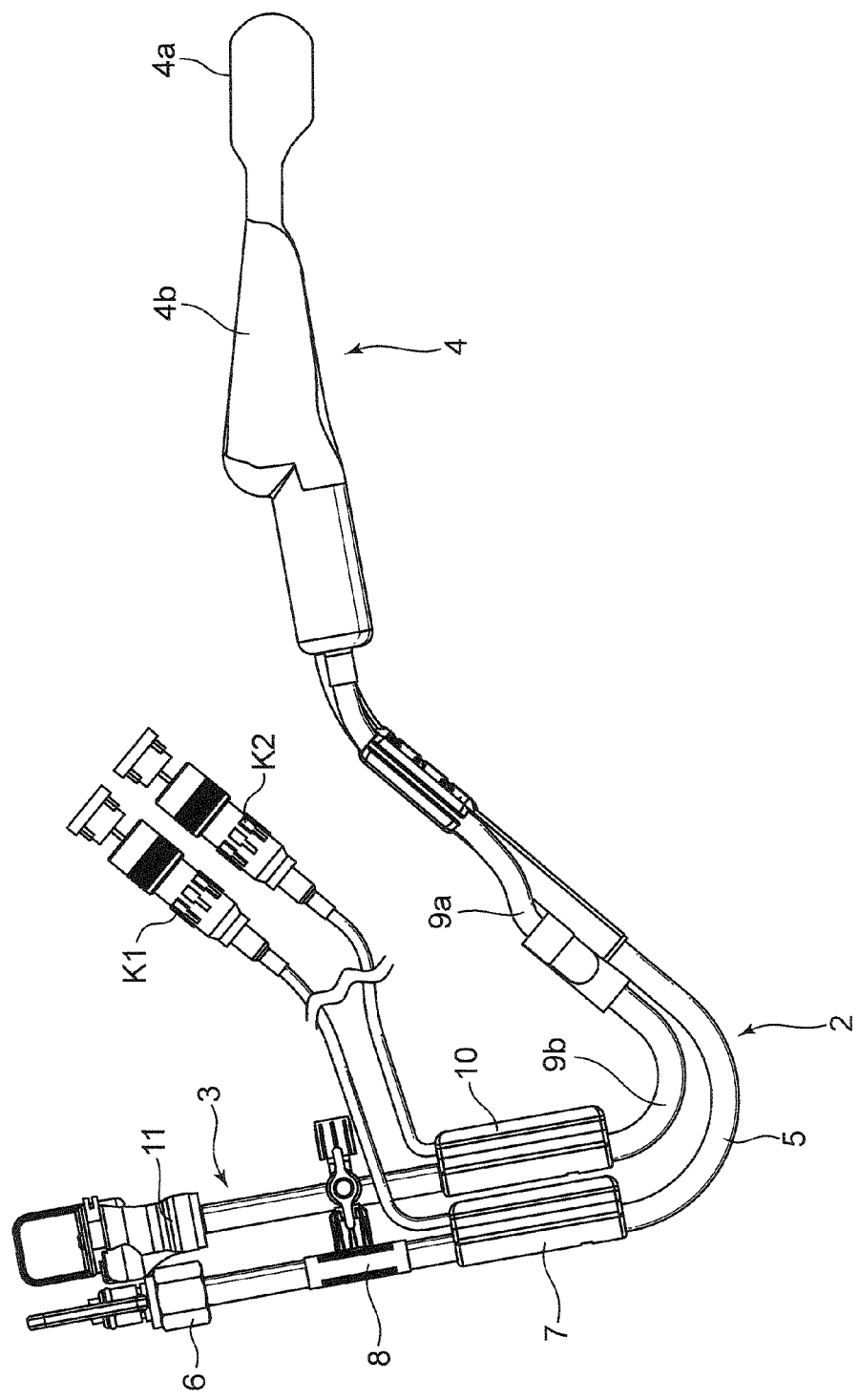
FIG. 1 is a side view depicting a general configuration of a brain cooling device according to an embodiment of the present invention.
Figure 2:
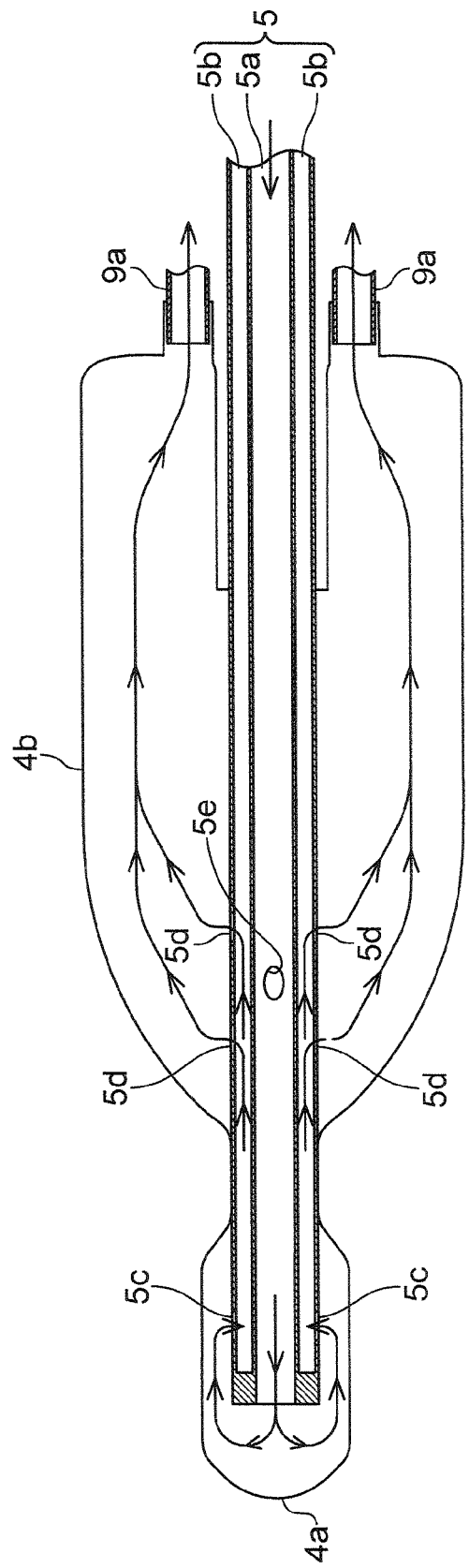
FIG. 2 is a schematic plan view depicting functions of the brain cooling device in FIG. 1.
Figure 3:
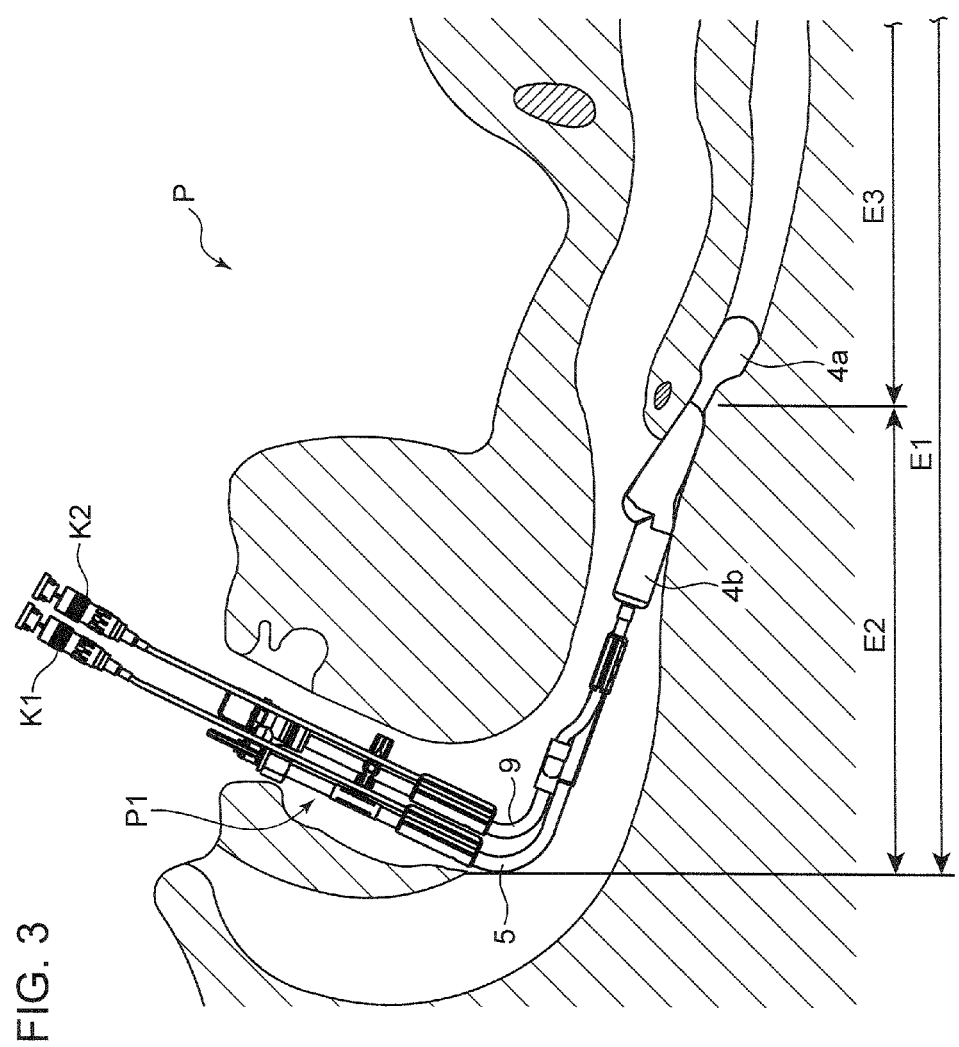
FIG. 3 is a schematic side view depicting a state of applying the brain cooling device in FIG. 1 to a patient.

FIG. 1 is a side view depicting a general configuration of a brain cooling device according to an embodiment of the present invention. FIG. 2 is a schematic plan view depicting functions of the brain cooling device in FIG. 1. FIG. 3 is a schematic side view depicting a state of applying the brain cooling device in FIG. 1 to a patient.

As FIG. 1 to FIG. 3 illustrate, a brain cooling device 1 has a cuff 4 inside in which fluid can be contained, and an injection unit 2, and an ejection unit 3 which are connected to the cuff 4 respectively.

The cuff 4 has an elasticity which allows it to have a shrunk form when the fluid inside is ejected, and an expanded form when the fluid is injected inside. The cuff 4 can be inserted into a patient P orally or transnasally in a shrunk state. The cuff 4 has a shape which allows it to be able to closely contact at least a part of an area E1 from an oral cavity P1 to a stomach (not illustrated) of the patient P by expanding in a state being inserted into the patient P. In concrete terms, the cuff 4 according to this embodiment closely contacts a lower portion of the area E1 of a pharynx of the patient P and an upper portion of an area E2 of an esophagus of the patient P, as shown in FIG. 3. In this description, the pharynx and the esophagus are assumed to be separated by an epiglottis (not illustrated) of the patient.

The cuff 4 has a tip cuff 4a disposed in the esophagus of the patient P, and a base cuff 4b disposed in the pharynx of the patient P. As illustrated in FIG. 2, the tip cuff 4a has a form of a bag so that fluid can be contained in a space between the tip cuff 4a and the outer side face of an injection tube 5 of an injection unit 2, which will be described later. In concrete terms, the tip cuff 4a is disposed such that the tip of the injection tube 5 is enclosed and the cuff 4a is glued onto the side face of the injection tube 5 at one location in the axis direction thereof. The base cuff 4b has a form of a bag so that fluid can be contained in sa space between the base cuff 4b and the side face of the injection tube 5 at a position closer to the base than the tip cuff 4a. In concrete terms, the base cuff 4b is disposed surrounding the injection tubes 5 and glued onto the side face of the injection tube 5 at two locations in the axis direction thereof.

The injection unit 2 has the injection tube 5 connected to the cuff 4, an injection side connector 6 disposed at the end of the injection tube 5 at the opposite side of the cuff 4, and a pressure sensor 7 and a two-way cock 8 which are disposed in an intermediate portion of the injection tube 5. As FIG. 2 illustrates, the injection tube 5 has three inner channels 5a, 5b and 5b, which are in parallel in the axis direction thereof. The inner channel 5a is a channel penetrating from the tip to the base of the injection tube 5. Each inner channel 5b is a channel of which tip and base are closed. Each inner channel 5b is connected to the tip cuff 4a via a side hole 5c which penetrates the side face of the injection tube 5, and is connected to the base cuff 4b via a side hole 5d which penetrates the side face of the injection tube 5. The injection side connector 6 is connected to the injection tube 5 so that fluid can be injected into the inner channel 5a. The fluid injected from the injection side connector 6 to the inner channel 5a is guided into the tip cuff 4a, is guided into each inner channel 5b via the side hole 5c, and is guided into the base cuff 4b via the side hole 5d. The pressure sensor 7 is a strain sensor that can detect the pressure of the fluid inside each inner channel 5b. This pressure sensor 7 can output an electric signal indicating the detection result to an external apparatus via a connector K1 (see FIG. 1). The two-way cock 8 has a connecting passage connecting each inner channel 5b and outside the injection tube 5, and a cock to open/close the connecting passage. The zero adjustment of the pressure sensor 7 can be performed by releasing the pressure of the fluid inside each inner channel 5a and 5b into the air using this two-way cock 8.

The ejection unit 3 has a pair of ejection tubes 9a connected to the base cuff 4b, a junction tube 9b for joining these ejection tubes 9a, an ejection side connector 11 disposed at the end of the junction tube 9b at the opposite side of the ejection tube 9a, and a pressure sensor 10 disposed in an intermediate portion of the junction tube 9b. The ejection tube 9a is connected to the base of the base cuff 4b, and can guide the fluid inside the base cuff 4b toward the junction tube 9b. The junction tube 9b is connected to each ejection tube 9a via a three-way connector, so as to merge the fluid guided by each ejection tube 9a. The pressure sensor 10 is a strain sensor that can detect the pressure of the fluid inside the junction tube 9b. This pressure sensor 10 can output an electric signal indicating the detection result to an external apparatus via a connector K2 (see FIG. 1). The ejection side connector 11 is connected to the junction tube 9b such that the fluid guided by the junction tube 9b can be ejected.

Now a method of using the brain cooling device 1 will be described with reference to FIG. 3.

First the cuff 4 in a shrunk state is orally inserted into a patient P until the tip cuff 4a is positioned in an upper portion of the area E3 of the esophagus of the patient P, and the base cuff 4b is positioned in a lower portion of the area E2 of the pharynx of the patient P. In this state, the cuff 4 is expanded by injecting cooled fluid from the injection side connector 6. Then as illustrated in FIG. 3, the cuff 4 closely contacts the pharynx and epiglottis of the patient P. If the brain cooling device 1 is filled with the fluid, fluid exceeding the capacitance is ejected from the ejection side connector 11 of the ejection unit 3. The ejected fluid is cooled down and injected into the injection side connector 6 again. By repeating this circulation, blood that flows through the carotid arteries located in the pharynx and the epiglottis of the patient P is cooled down, and this cooled blood, transported to the brain, cools down the brain.

Now a brain cooling apparatus that circulates the fluid for the above mentioned brain cooling device 1 will be described.

Figure 4:
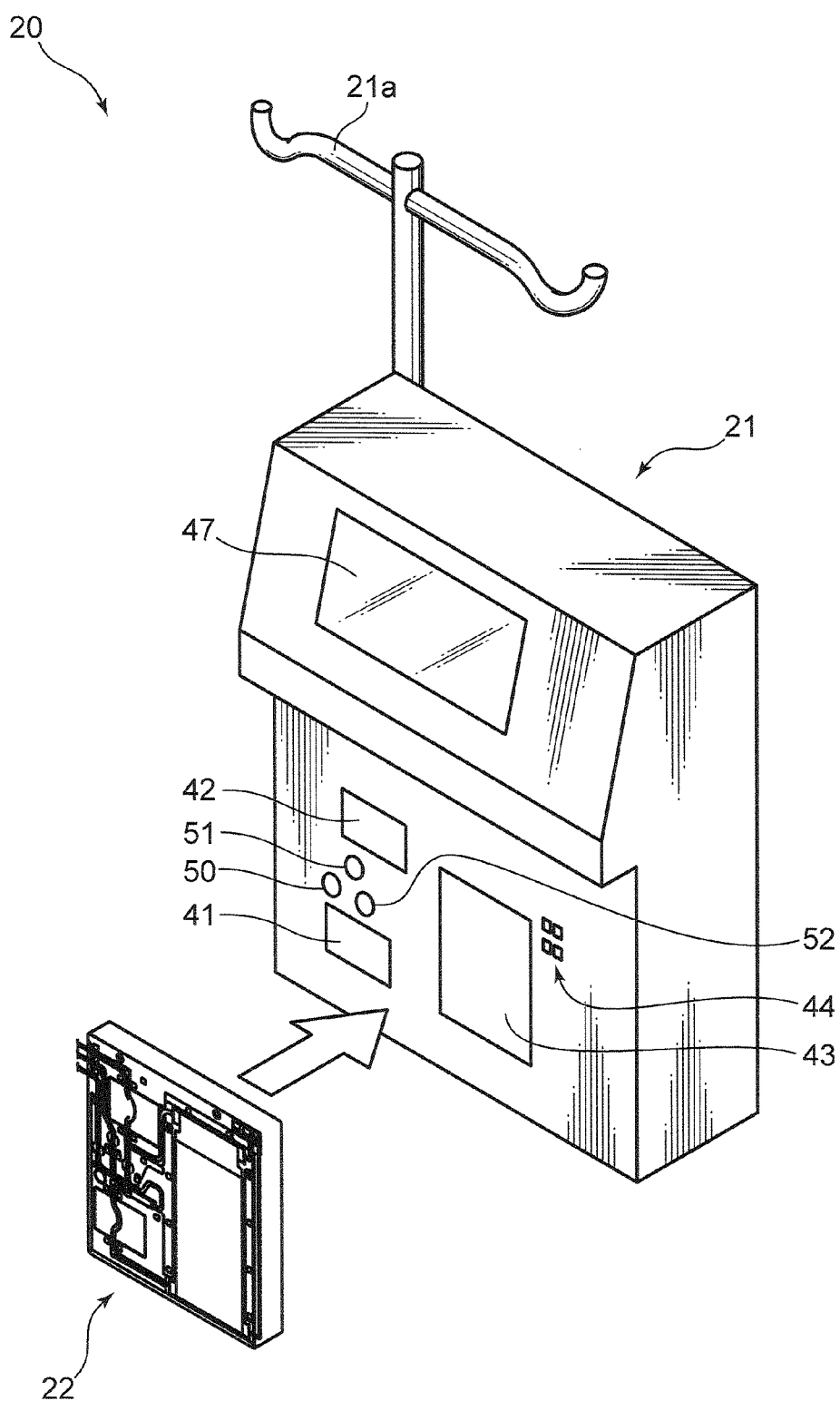
FIG. 4 is a perspective view depicting a general configuration of a brain cooling apparatus according to an embodiment of the present invention.
Figure 5:
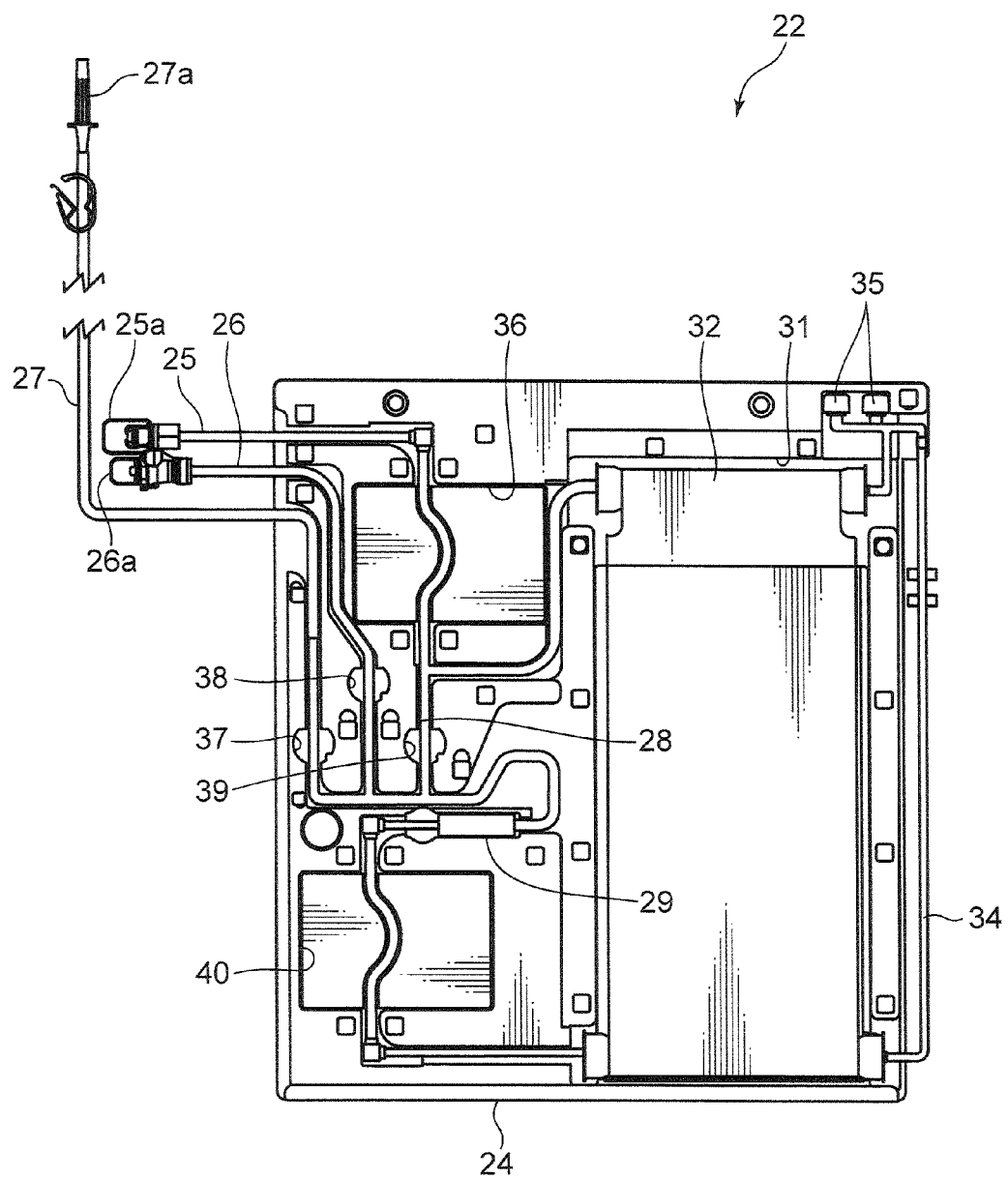
FIG. 5 is a front view depicting a fluid filled unit of the cooling apparatus in FIG. 4.
Figure 6:
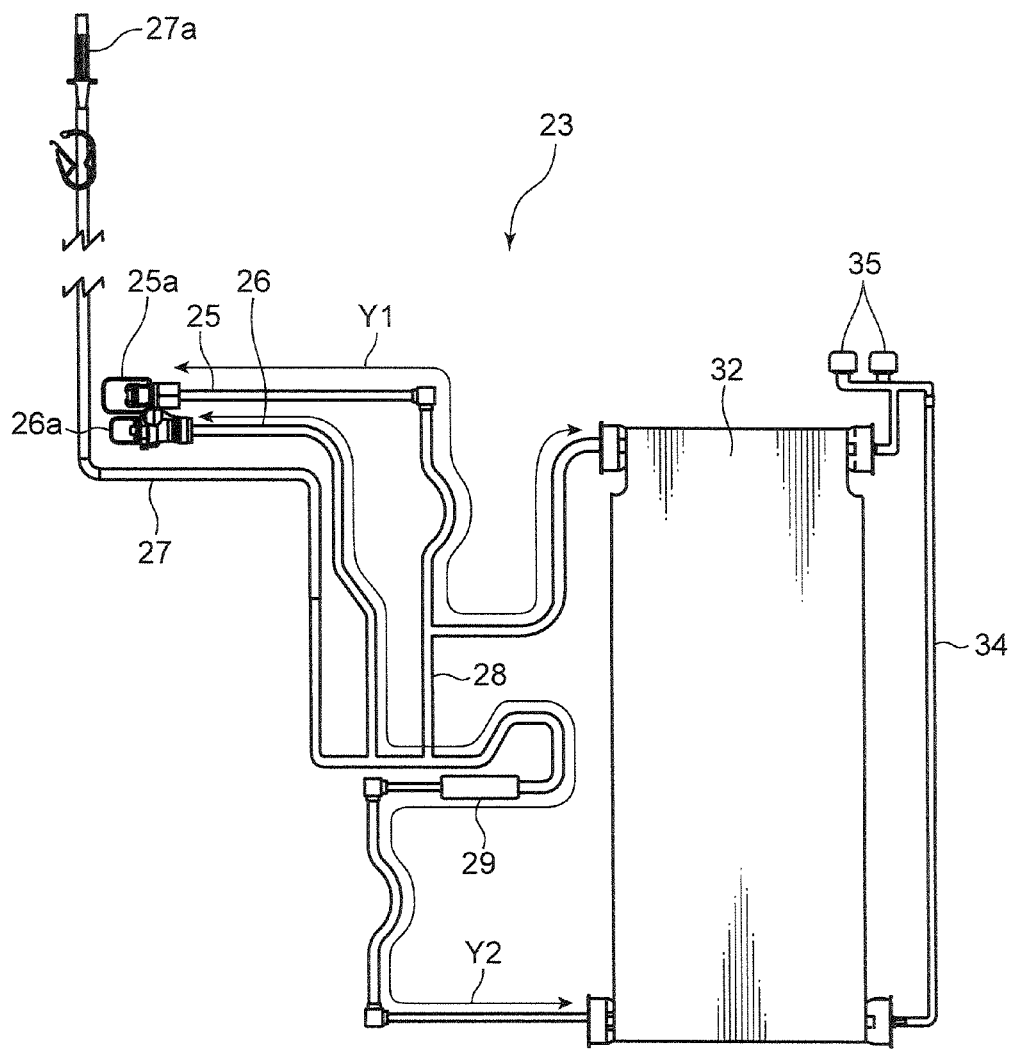
FIG. 6 is a front view when a channel portion in FIG. 5 is enlarged.

FIG. 4 is a perspective view depicting a general configuration of the brain cooling apparatus according to an embodiment of the present invention. FIG. 5 is a front view depicting a fluid filled unit of the cooling apparatus in FIG. 4. FIG. 6 is a front view when the channel portion in FIG. 5 is enlarged.

As FIG. 4 to FIG. 6 illustrate, the brain cooling apparatus 20 has a fluid filled unit 22 that is connected to the brain cooling device 1, and an apparatus main unit 21 that circulates fluid filled in the fluid filled unit 22. The fluid filled unit 22 is able to be attached to/removed from the apparatus main unit 21, and is removed from the apparatus main unit 21 and disposed after being used for a specific patient. A concrete configuration will now be described.

The fluid filled unit 22 has a channel member 23 (see FIG. 6) constituting a circulation route of the fluid for the brain cooling device 1, and a frame member 24 (see FIG. 5) which holds the channel member 23 in a predetermined form, and is attached to/removed from the apparatus main unit 21.

The channel member 23 has a supply tube (supply channel) 26 that is connected to the injection tube 5 (see FIG. 1) of the brain cooling device 1, a collection tube (collection channel) 25 that is connected to the junction tube 9b of the brain cooling device 1, a storage tank (storage unit) 32 that is connected to the supply tube 26 and the collection tube 25, a bypass tube (bypass channel) 28 that connects the supply tube 26 and the collection tube 25, a detection tube 34 that connects an upper portion and a lower portion of the storage tank 32, an air vent filter 35 disposed on the detection tube 34, a filling tube 27 that is connected to an intermediate portion of the supply tube 26, and a temperature/pressure sensor 29 that is disposed in an intermediate portion of the supply tube 26. The supply tube 26 has an injection side connection tube 26a which can be attached to/removed from the injection side connector 6 of the brain cooling device 1. This supply tube 26 is disposed between the injection side connection unit 26a and the storage tank 32, as indicated by an arrow Y2 in FIG. 6. The supply tube 26 is connected to the storage tank 32 at a position lower than the level of the fluid stored in the storage tank 32. The collection tube 25 has an ejection side connection unit 25a which can be attached to/removed from the ejection side connector 11 of the brain cooling device 1. The collection tube 25 is disposed between the ejection side connection unit 25a and the storage tank 32, as indicated by the arrow Y1 in FIG. 6. The collection tube 25 is connected to the storage tank 32 at a position higher than the level of the fluid stored in the storage tank 32. The bypass tube 28 is connected to both tubes 25 and 26, so as to connect the intermediate portion of the supply tube 26 and the intermediate portion of the collection tube 25. The storage tank 32 is a container made of synthetic resin, that can be filled with 500 ml of physiological saline solution as the fluid. If the physiological saline solution is filled into the storage tank 32, the physiological saline fluid is injected into the detection tube 34 corresponding to the level of the physiological saline solution in the storage tank 32. The air vent filter 35 is provided for releasing the area inside the storage tank 32 into the air. In concrete terms, the air vent filter 35 allows gas to pass through, but interrupts the passing of liquid. The filling tube 27 is connected to the supply tube 26 at a position between the injection side connection unit 26a and the bypass tube 28. A piercing unit 27a, that can pierce a port unit of a medicine bag containing physiological saline solution, is disposed on the edge of the filling tube 27. The temperature/pressure sensor 29 is disposed in an intermediate portion of the supply tube 26 located between the bypass tube 28 and the storage tank 32. This temperature/pressure sensor 29 can detect the temperature and pressure of the physiological saline solution in the supply tube 26, and can output an electric signal to indicate this detection value to the apparatus main unit 21.

The frame member 24 is a plate member made of synthetic resin for holding the channel member 23 in the form shown in FIG. 6. In the frame member 24, as FIG. 5 illustrates, a tank hole 31, a pump hole 36, a pump hole 40, a valve hole 37, a valve hole 38 and a valve hole 39 are formed, penetrating from the front face to the rear face. The storage tank 32 is inserted into the tank hole 31. In other words, the storage tank 32 is held by the frame member 24 in a state where the front face and the rear face thereof are exposed. The pump hole 36 is disposed in a position where the collection tube 25 crosses vertically. In concrete terms, the intermediate portion of the collection tube 25, located between the bypass tube 28 and the ejection side connection unit 25a, crosses the pump hole 36 on the front face side of the frame member 24. The pump hole 40 is disposed in a position where the supply tube 26 crosses vertically. In concrete terms, the intermediate portion of the supply tube 26, located between the temperature/pressure sensor 29 and the storage tank 32, crosses the pump hole 40 on the front face side of the frame member 24. The valve hole 37 is disposed in a position where the filling tube 27 crosses vertically. The valve hole 38 is disposed in a position where the intermediate portion of the supply tube 26 crosses vertically. In concrete terms, the intermediate portion of the supply tube 26, located between the bypass tube 28 and the injection side connection unit 26a, crosses the valve hole 38 on the front face of the frame member 24. The valve hole 39 is disposed in a position where the intermediate portion of the bypass tube 28 crosses vertically.

Figure 7:
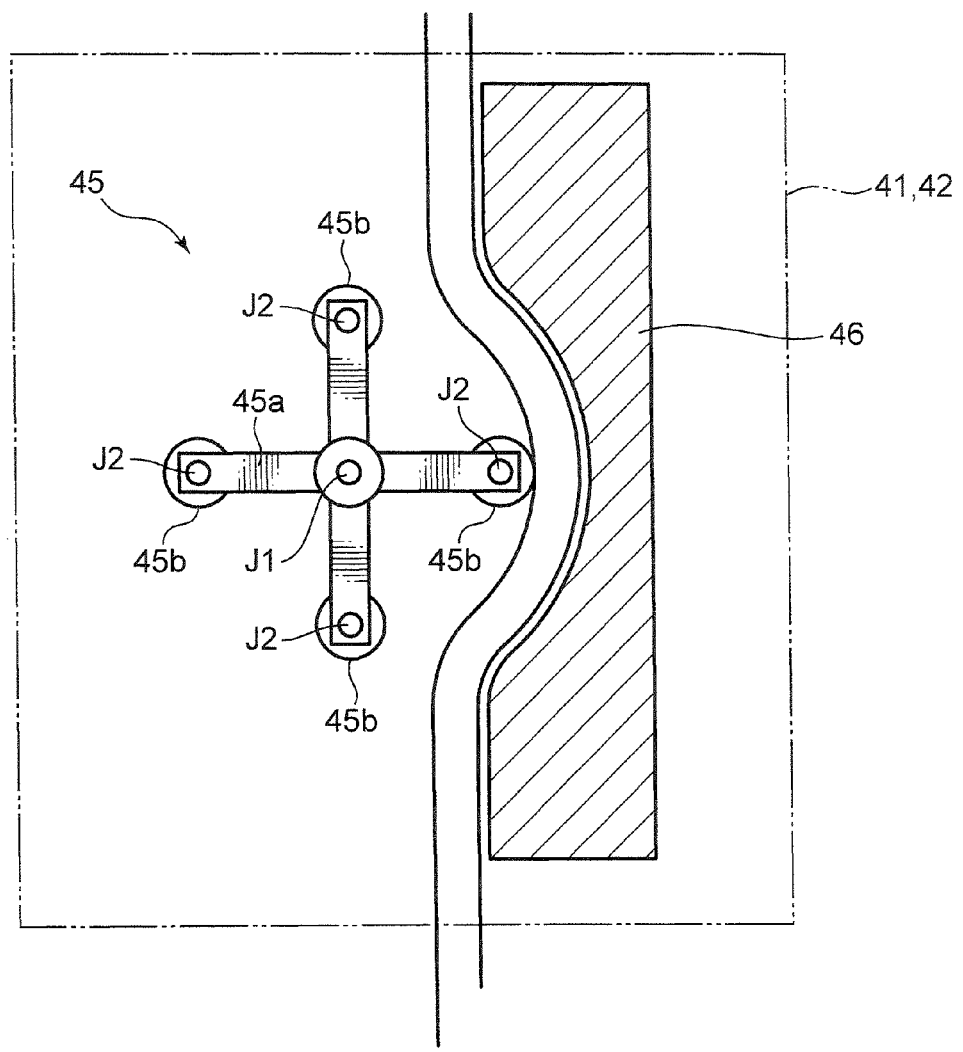
FIG. 7 is a schematic diagram depicting the functions of a first pump and a second pump in FIG. 4.

As FIG. 4 and FIG. 5 illustrate, the apparatus main unit 21 has a first pump 41, a second pump 42, a cooling member 43, a level sensor 44, a first valve 50, a second valve 51, a third valve 52, an operation unit 47 and a control device (see FIG. 8) 48. The first pump 41 is for flowing the fluid inside the supply tube 26 along the supply tube 26. In concrete terms, the first pump 41 is disposed in the pump hole 40 when the fluid filled unit 22 is attached to the apparatus main unit 21. The second pump 42 is for flowing the fluid inside the collection tube 25 along the collection tube 25. In concrete terms, the second pump 42 is disposed in the pump hole 36 when the fluid filled unit 22 is attached to the apparatus main unit 21. The configuration of these pumps 41 and 42 will be described with reference to FIG. 7. FIG. 7 is a schematic diagram depicting the functions of the first pump 41 and the second pump 42 in FIG. 4.

As FIG. 7 illustrates, the pump 41 or 42 has a tube support member 46, and a rotator 45 for pressing the tube by sandwiching the tube with the tube support member 46. The rotator 45 has a cross-shaped rotation frame 45a which has four arms, and a roller 45b which is disposed at the tip of each arm of the rotation frame 45a respectively. The rotation frame 45a can rotate around the axis J1. The roller 45b is supported by each arm rotatably around the axis J2 that is parallel with the axis J1, in a state of a part of the roller 45b protruding from the tip of the arm of the rotation frame 45a. The tube support member 46 has an arc-shaped groove of which center is located in the axis J1, and the tube is inserted along the inner side wall of this groove. The rotator 45 is disposed so that the tube is sandwiched between the tube support member 46 and the rotator 45. If the rotation frame 45a is driven and rotated around the axis J1 by a motor (not illustrated), the roller 45b rotates while maintaining the state of the tube being sandwiched between the roller 45b and the tube support member 46, whereby the fluid in the tube flows in the rotation direction. Since the roller 45b rotates while sandwiching the tube like this, the flow of the fluid in the tube is restricted when the rotation of the rotation frame 45a stops.

Referring back to FIG. 4 and FIG. 5, the cooling member 43 closely contacts the storage tank 32 and cools the fluid in the storage tank 32. In concrete terms, the cooling member 43 exerts the cooling capability according to the voltage to be applied, for which a Peletier element, for example, can be used. The cooling member 43 is disposed in a position that allows the cooling member 43 to closely contact the storage tank 32 when the fluid filled unit 22 is attached to the apparatus main unit 21. The apparatus main unit 21 has a cover that can be closed so as to sandwich the attached fluid filled unit 22, and a cooling member 43 is also disposed in the cover, although the cover is omitted in FIG. 4. The level sensor 44 is for detecting the level of the fluid in the storage tank 32. In concrete terms, the level sensor 44 is constituted by an infrared sensor, which is located at both sides of the detection tube 34 so as to sandwich the detection tube 34 when the fluid filled unit 22 is attached to the apparatus main unit 21. The first valve 50 interrupts or releases the filling tube 27. In concrete terms, the first valve 50 is disposed at both sides of the filling tube 27 via the valve hole 37 so as to sandwich the filling tube 27 when the fluid filled unit 22 is attached to the apparatus main unit 21. The first valve 50 constricts the filling tube 27 as voltage is applied, and stops the constriction when voltage is not applied. The second valve 51 interrupts or releases the collection tube 25. The third valve 52 interrupts or releases the supply tube 26. Description of the second valve 51 and the third valve 52, which have a same configuration as the first valve 50, is omitted.

The operation unit 47 has a role of a display unit for displaying operation state and other information, and a role of an operation unit for inputting various setting items to the later mentioned control device 48. In concrete terms, the operation unit 47 can be constituted by a touch panel.

Figure 8:
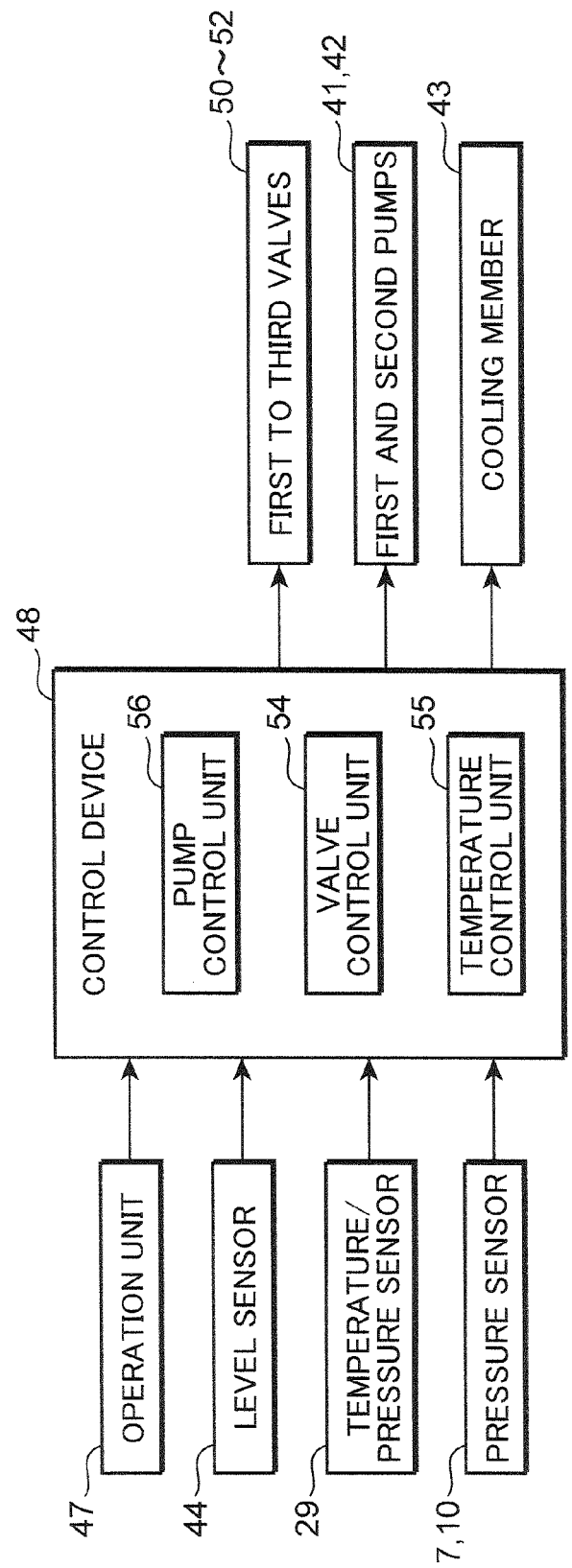
FIG. 8 is a block diagram depicting an electric configuration of a control device of the apparatus main unit in FIG. 4.

FIG. 8 is a block diagram depicting an electric configuration of the control device 48 of the apparatus main unit 21 in FIG. 4.

The control device 48 controls the driving of the first valve 50 to the third valve 52, the first pump 41 and the second pump 42, and the cooling member 43 based on the input signals from the control unit 47, the level sensor 44, the temperature/pressure sensor 29 and the pressure sensors 7 and 10 (see FIG. 1). In concrete terms, the control device 48 has a pump control unit 56 for controlling the driving of the first pump 41 and the second pump 42, a valve control unit 54 for controlling the driving of the first valve 50 to the third valve 52, and a temperature control unit 55 for adjusting the cooling capability by the cooling member 43.

Figure 9:
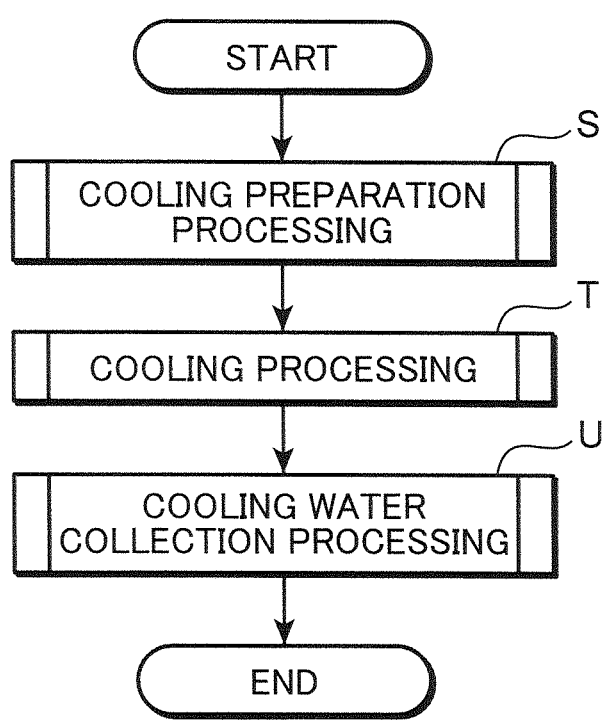
FIG. 9 is a flow chart depicting a basic processing executed by the control device in FIG. 8.
Figure 10:
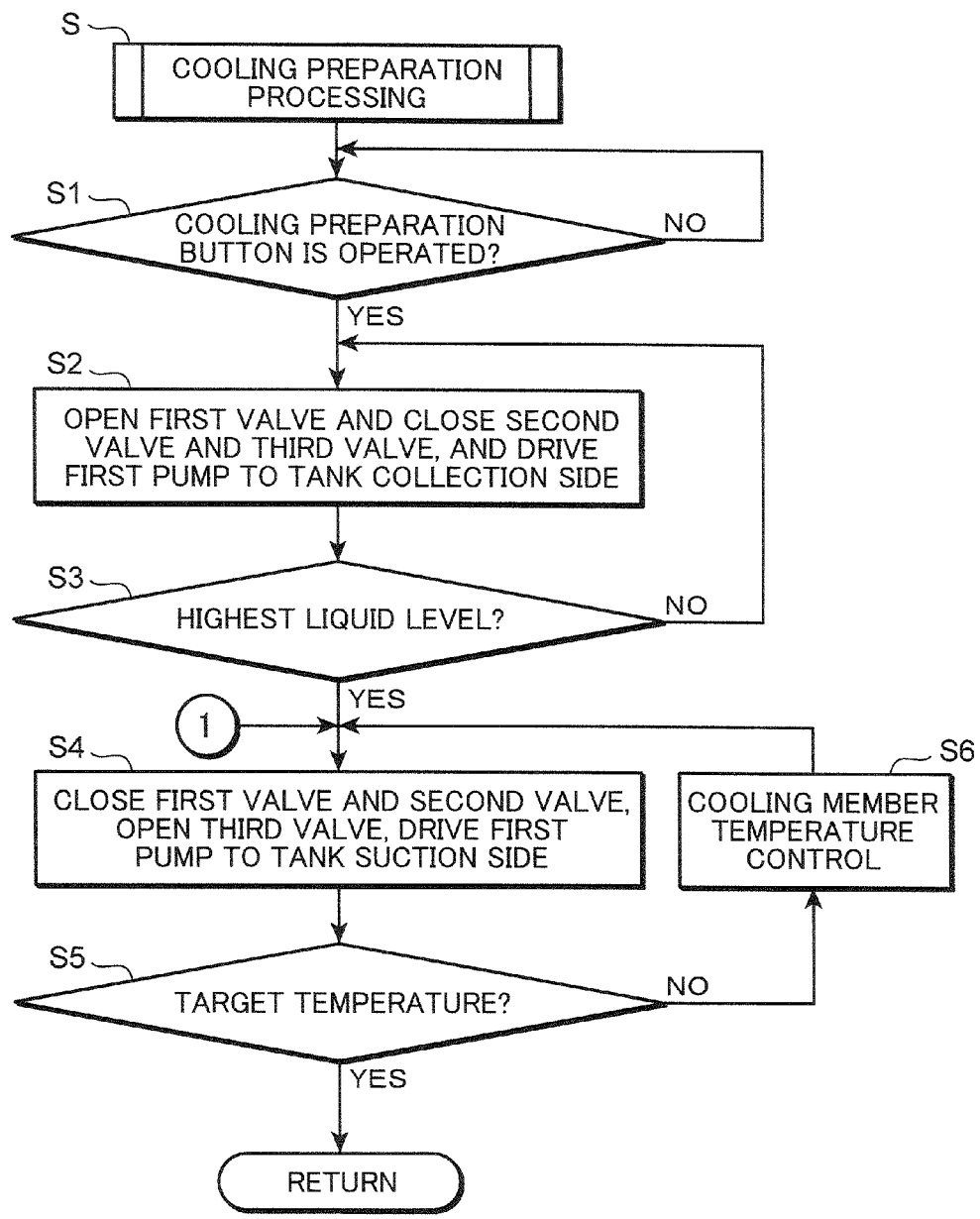
FIG. 10 is a flow chart depicting the cooling preparation processing in FIG. 9.
Figure 11:
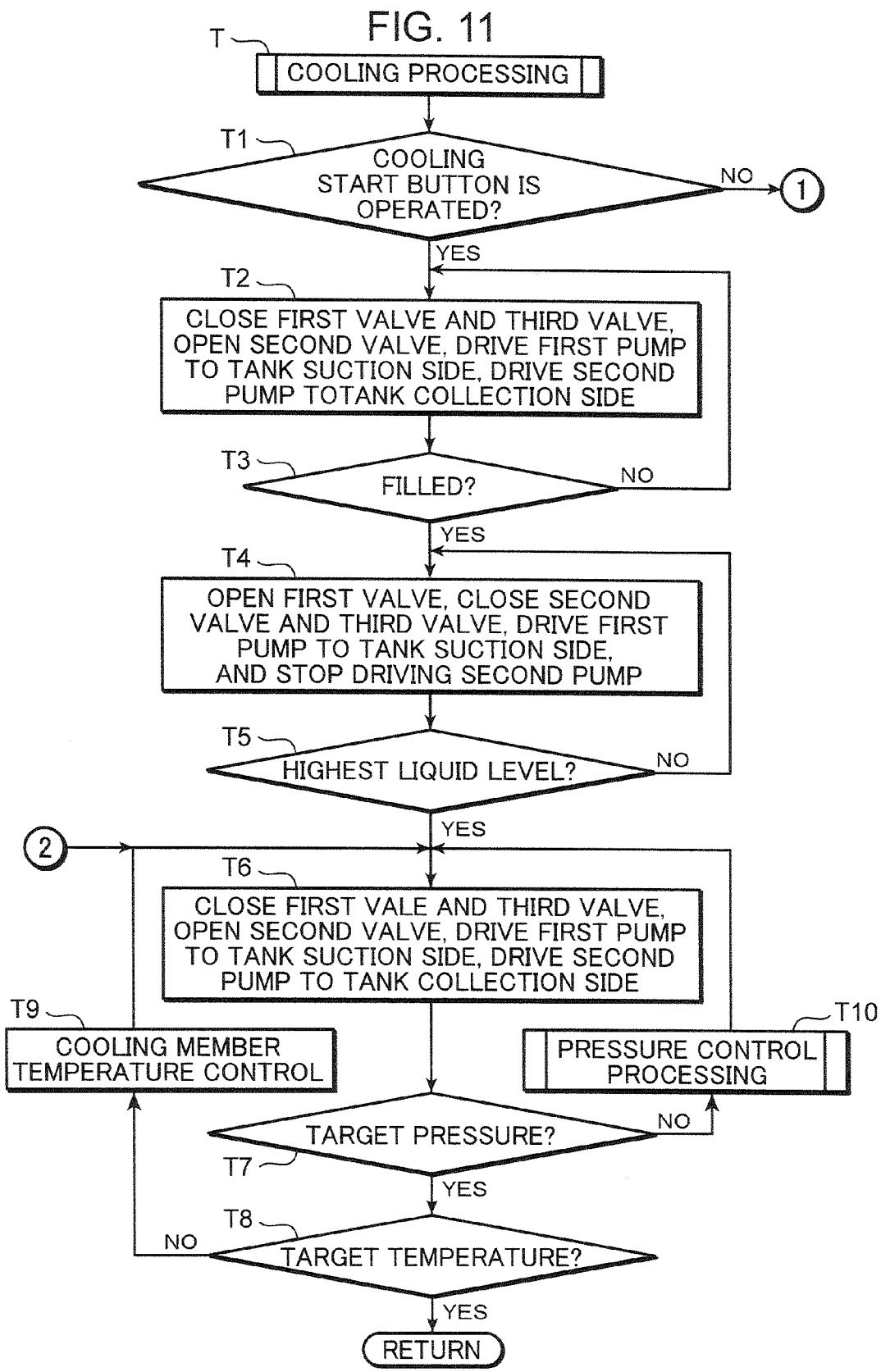
FIG. 11 is a flow chart depicting the cooling processing in FIG. 9.
Figure 12:
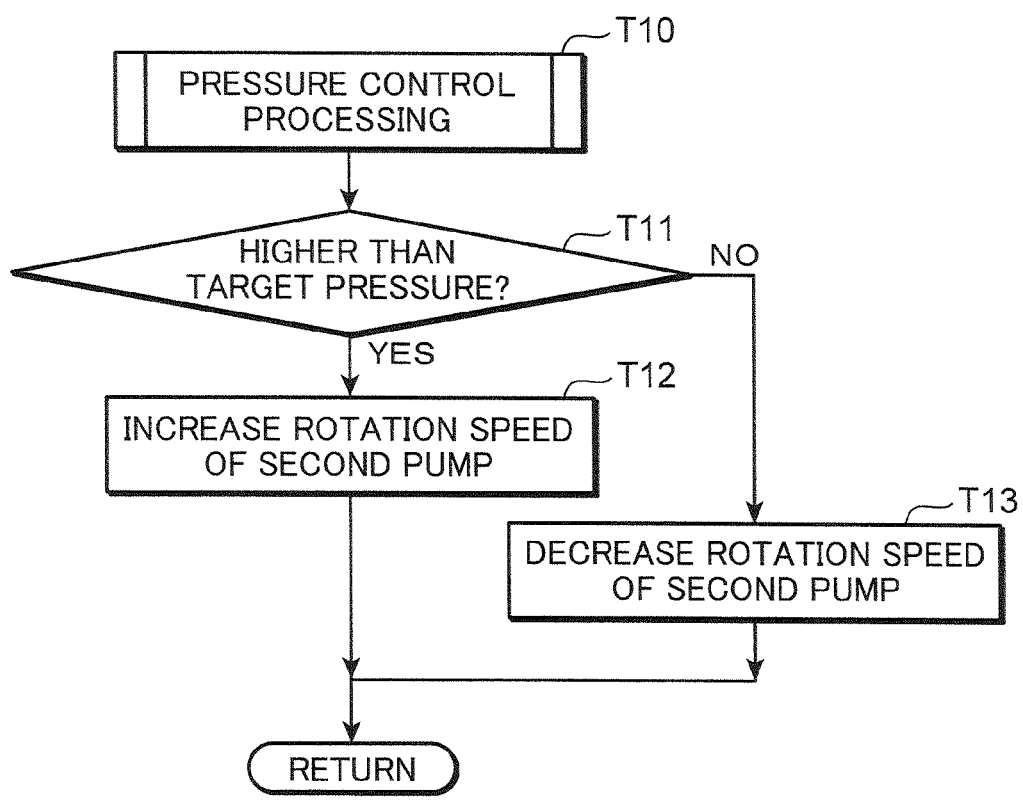
FIG. 12 is a flow chart depicting the pressure control processing in FIG. 11.
Figure 13:
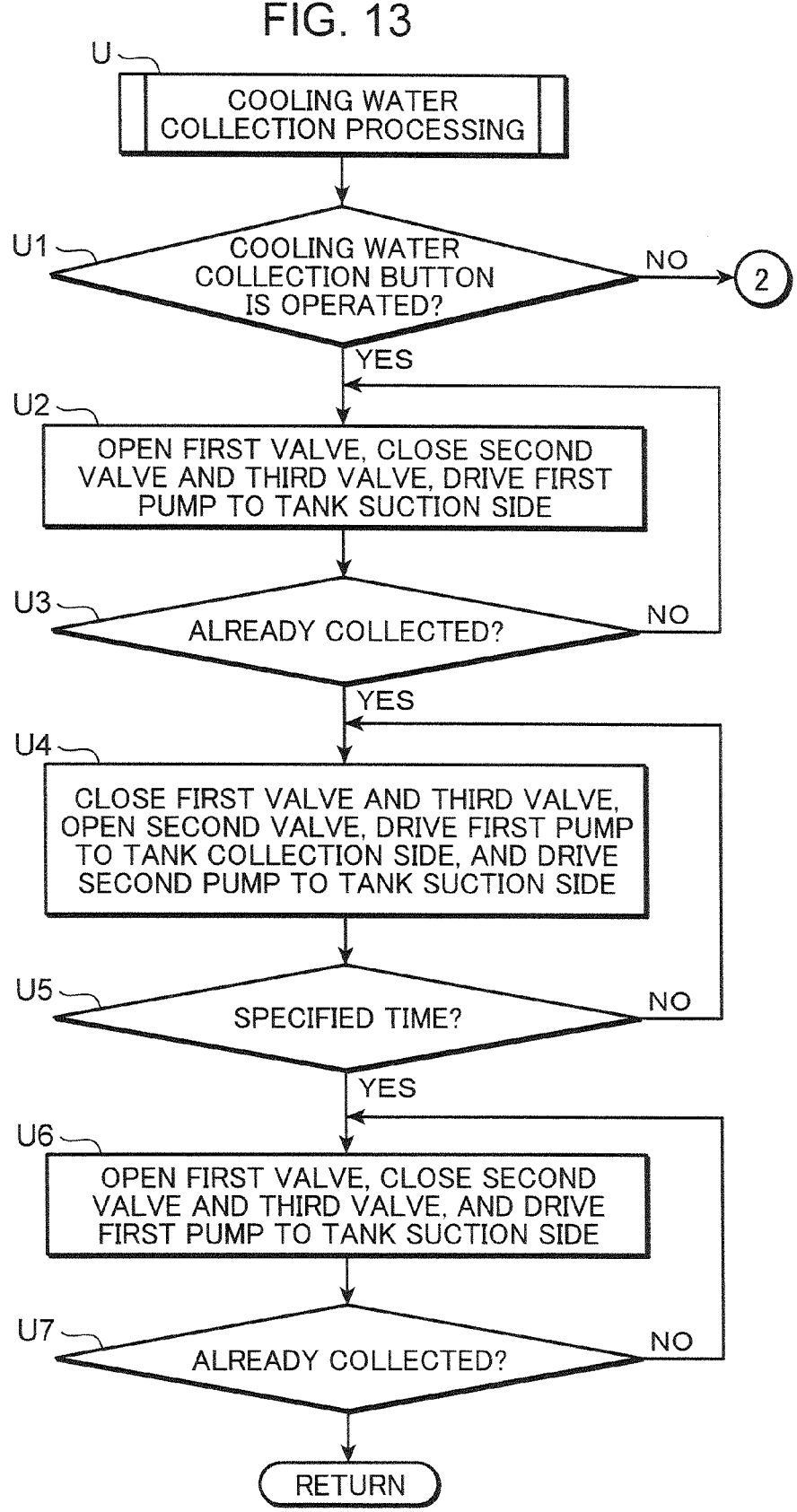
FIG. 13 is a flow chart depicting the cooling water collection processing in FIG. 9.

Processing executed by the control device 48 will now be described with reference to FIG. 9 to FIG. 13. FIG. 9 is a flow chart depicting a basic processing executed by the control device 48 in FIG. 8. FIG. 10 is a flow chart depicting the cooling preparation processing in FIG. 9. FIG. 11 is a flow chart depicting the cooling processing in FIG. 9. FIG. 12 is a flow chart depicting the pressure control processing in FIG. 11. FIG. 13 is a flow chart depicting the cooling water collection processing in FIG. 9.

As a general flow, the control device 48 sequentially executes the cooling preparation processing S, the cooling processing T and the cooling water collection processing U, as shown in FIG. 9.

Before executing the cooling preparation processing S, a medical staff performs the following preparation. In concrete terms, the medical staff attaches the fluid filled unit 22 to the apparatus main unit 21 as illustrated in FIG. 4, and uses the piercing portion 27a (see FIG. 5) of the fluid filled unit 22 to pierce a port of the bag (not illustrated) filled with physiological saline solution. In this state, the medical staff hangs the bag onto a hanging hook 21a of the apparatus main unit.

As FIG. 10 shows, in the cooling preparation processing S, it is determined whether the medical staff operated an operation preparation button displayed on the operation unit 47 (step S1), and if it is determined that the operation preparation button was not operated, step S1 is repeatedly executed.

Figure 15:
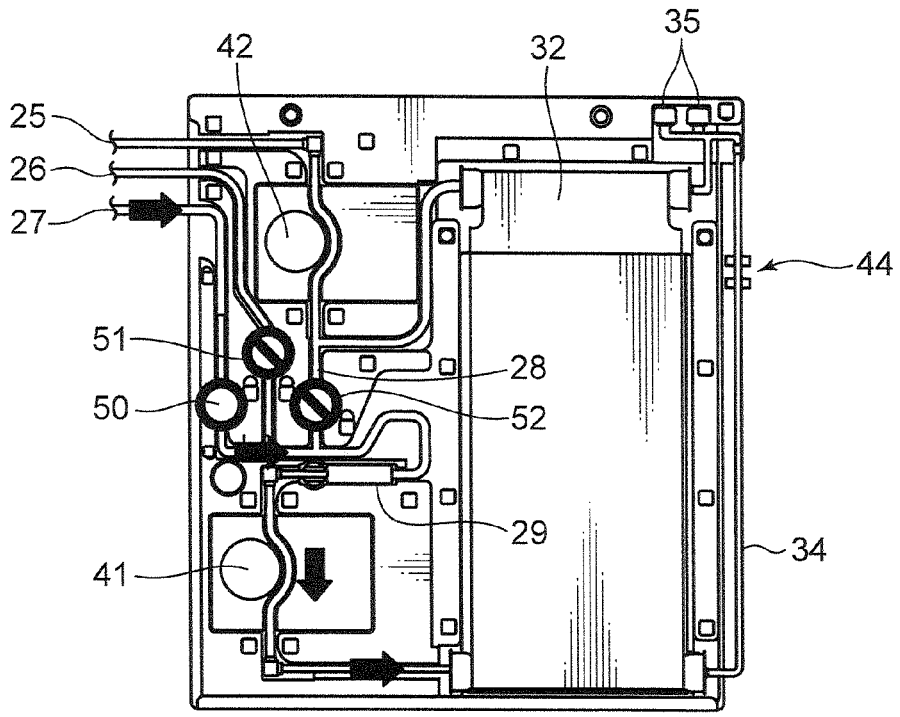
FIG. 15 is a front view depicting a state of filling the physiological saline solution from a bag into a storage tank.

If it is determined that the operation button was operated in step S1, filling of the physiological saline solution into the storage tank 32 is started in step S2. In other words, as FIG. 15 illustrates, the filling tube 27 is opened by the first valve 50, and the supply tube 26 and the collection tube 25 are interrupted by the second valve 51 and the third valve 52. Further, the first pump 41 is driven in a direction of the physiological saline solution flowing toward the storage tank 32. Thereby the physiological saline solution in the bag is guided to the storage tank 32 via the filling tube 27 and the supply tube 26.

Then it is determined whether the level of the physiological saline solution in the storage tank 32 is the preset highest level by the level sensor 44 (step S3), and if it is determined that the level is not the highest level, step S2 is repeated.

Figure 16:
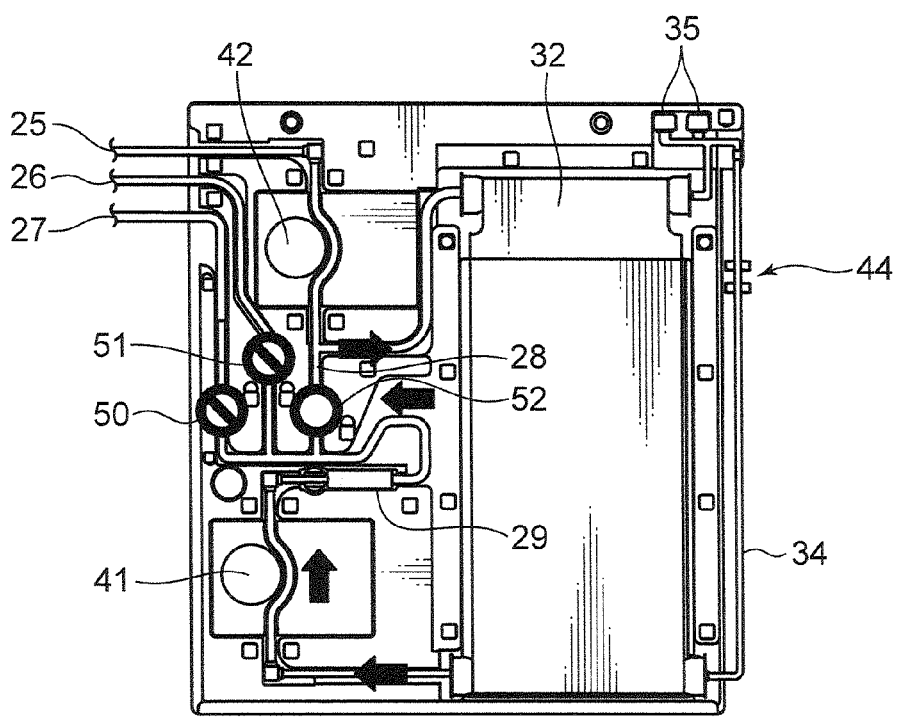
FIG. 16 is a front view depicting a state of circulating the physiological saline solution in the storage tank inside the cooling apparatus.

If it is determined that the level of the physiological saline solution in the storage tank 32 is the highest level in step S3, cooling of the physiological saline solution in the storage tank 32 is started in step S4. In other words, as FIG. 16 illustrates, the filling tube 27 and the supply tube 26 are interrupted by the first valve 50 and the second valve 51, and the bypass tube 28 is opened by the third valve 52. In this state, the first pump 41 is driven in the direction of the physiological saline solution being sucked from the storage tank 32, and voltage is applied to the cooling member 43 (see FIG. 8).

Then it is determined whether the temperature of the physiological saline solution detected by the temperature/pressure sensor 29 is a target temperature (step S5). If it is determined that the temperature of the physiological saline solution is not the target temperature, the temperature of the cooling member 43 is controlled (step S6). Specifically, in step S6, if the temperature of the physiological saline solution is higher than the target temperature, the voltage to be applied to the cooling member 43 is increased to increase the cooling capability of the cooling member 43. If the temperature of the physiological saline solution is lower than the target temperature, the voltage to be applied to the cooling member 43 is decreased to decrease the cooling capability of the cooling member 43.

If it is determined that the temperature of the physiological saline solution is the target temperature in step S6, then processing returns to the main routine in FIG. 9, and the cooling processing T in FIG. 11 is executed.

Prior to the execution of this cooling processing T, the medical staff connects the injection side connector 6 of the brain cooling device 1 in FIG. 1 to the injection side connection unit 26a of the fluid filled unit 22 in FIG. 5, and connects the ejection side connector 11 of the brain cooling device 1 in FIG. 1 to the ejection side connection unit 25a of the fluid filled unit 22 in FIG. 5. These connections may be made via predetermined extension tubes between the brain cooling device 1 and the fluid filled unit 22.

As FIG. 11 shows, in the cooling processing T, it is determined whether the medical staff operated a cooling start button displayed on the operation unit 47 (step T1). If it is determined that the cooling start button was not operated, step S4 is repeatedly executed.

Figure 17:
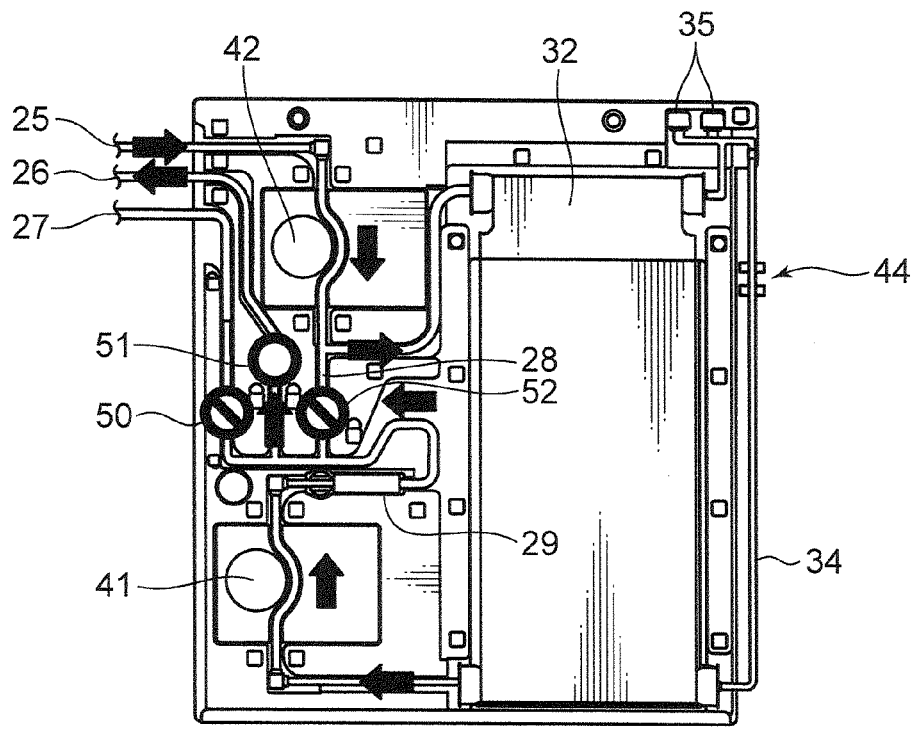
FIG. 17 is a front view depicting a state of circulating the physiological saline solution between the storage tank and the cuff of the cooling device.

If it is determined that the cooling start button was operated in step T1, filling of the physiological saline solution into the brain cooling device 1 is started in step T2. In other words, as FIG. 17 illustrates, the filling tube 27 and the bypass tube 28 are interrupted by the first valve 50 and the third valve 52, and the supply tube 26 is opened by the second valve 51. Further, the first pump 41 is driven in a direction of the physiological saline solution being sucked from the storage tank 32, and the second pump 42 is driven so that a flow toward the storage tank 32 is generated. Thereby the physiological saline solution in the storage tank 32 is supplied to the brain cooling device 1 via the supply tube 26, and excessive physiological saline that cannot be contained in the brain cooling device 1 is collected in the storage tank 32 via the collection tube 25.

Figure 14:
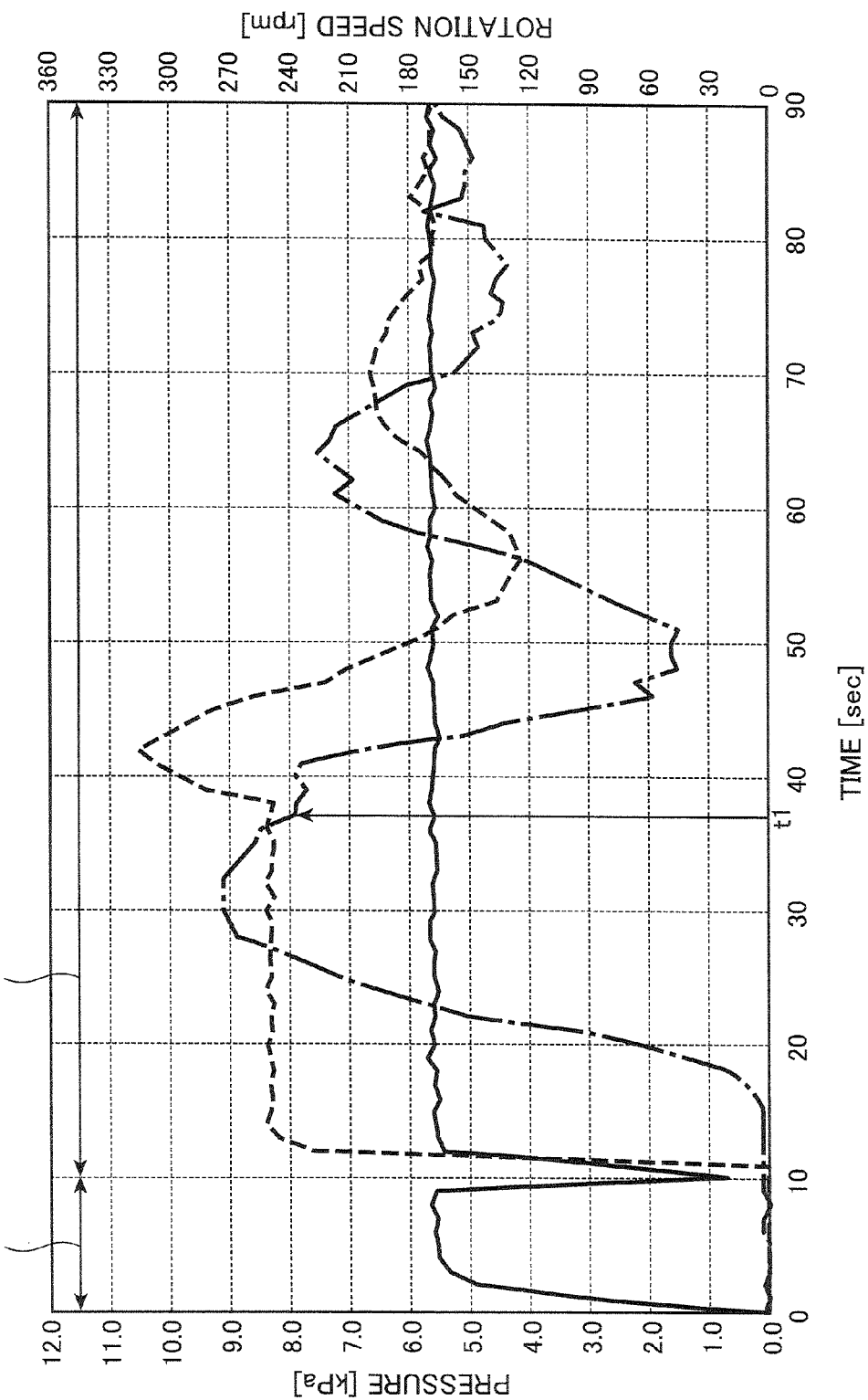
FIG. 14 is a graph depicting a transition of the rotation speed of each pump and the pressure detected by the pressure sensor in the cooling preparation processing S and the cooling processing T.

Then it is determined whether the physiological saline solution was filled into the brain cooling device 1 based on the pressure detected by the pressure sensor 10 of the brain cooling device 1 (step T3). Now this determination will be described with reference to FIG. 14. FIG. 14 is a graph depicting a transition of the rotation speed of each pump and the pressure detected by the pressure sensor 10 in the cooling preparation processing S and the cooling processing T. In FIG. 14, the solid line indicates the rotation speed of the first pump 41, the broken line is the rotation speed of the second pump 42, and the dashed-dotted line is the pressure detected by the pressure sensor 10. As the time t1 in FIG. 14 indicates, it is confirmed experimentally that the pressure detected by the pressure sensor 10 drops to about 1 kPa if the air in the brain cooling device 1 is replaced with the physiological saline solution. Therefore in step T3, it is determined whether the physiological saline solution is filled into the brain cooling device 1 depending on whether the pressure detected by the pressure sensor 10 dropped. If it is determined that the physiological saline solution is not filled in step T3, step T2 is repeatedly executed.

If it is determined that the physiological saline solution is filled into the brain cooling device 1 in step T2, the physiological saline solution is replenished from the bag containing the physiological saline solution to the storage tank 32 in step T4. In other words, as FIG. 15 illustrates, the first valve 50 is set to the open state and the second valve 51 and the third valve 52 are set to the close state, and the first pump 41 is driven in a direction of generating the flow to the storage tank 32. Thereby the physiological saline solution is guided from the bag toward the storage tank 32.

Then it is determined whether the level of the physiological saline solution in the storage tank 32 is the highest level (step T5). If it is determined that the level is not the highest level, step T4 is repeatedly executed.

If it is determined that the level is the highest level in step T5, circulation of the physiological saline solution between the storage tank 32 and the water cooling device 1 is started, as shown in FIG. 17 (step T6). Specifically, in step T6, the filling tube 27 and the bypass tube 28 are interrupted by the first valve 50 and the third valve 52, and the supply tube 26 is opened by the second valve 51. In this state, the first pump 41 is driven in a direction of sucking the physiological saline solution from the storage tank 32, and the second pump 42 is driven in a direction of collecting the physiological saline solution in the storage tank 32.

Then it is determined whether the pressure of the physiological saline solution in the brain cooling device 1 detected by the pressure sensor 10 is a preset target pressure (e.g. 5 kPa) (step T7). If it is determined that the pressure detected by the pressure sensor 10 is not the target pressure, the pressure control processing T10 is executed. The target pressure may be a specific numerical value, but may also be set as a predetermined range. FIG. 12 is a flow chart depicting the content of the pressure control processing T10 in FIG. 11.

As FIG. 12 shows, when the pressure control processing T10 is started, it is determined whether the pressure detected by the pressure sensor 10 is higher than the target pressure (step T11). If the pressure detected by the pressure sensor 10 is higher than the target pressure, the rotation speed of the second pump 42 is increased (step T12). If the pressure detected by the pressure sensor 10 is lower than the target pressure, the rotation speed of the second pump 42 is decreased (step T13). In other words, according to the cooling processing of this embodiment, the rotation speed of the second pump 42 is increased when the pressure detected by the pressure sensor 10 exceeds the target pressure, and the rotation speed of the second pump 42 is decreased when the pressure detected by the pressure sensor 10 does not reach the target pressure, while keeping the rotation speed of the first pump 41 approximately constant, as shown in FIG. 14. The rotation speed of the first pump 41 is approximately constant in this embodiment, but the present invention is not limited to this, and rotation may be controlled not only for the second pump 42 but also for the first pump 41. However the rotation speed of the first pump 41 is preferably fixed if the flow rate must be uniform, since the flow rate of the physiological saline solution to the brain cooling device 1 is determined by the rotation speed of the first pump 41.

Referring back to FIG. 11, if it is determined that the pressure detected by the pressure sensor 10 is the target pressure in step T7, it is determined whether the temperature of the physiological saline solution detected by the temperature/pressure sensor 29 is a preset target temperature (step T8).

If it is determined that the temperature of the physiological saline solution is not the target temperature, the temperature of the cooling member 43 is controlled, just like the above mentioned step S6, and step T6 is repeatedly executed. If it is determined that the temperature of the physiological saline solution is the target temperature in step T8, then processing returns to FIG. 9 and the cooling water collection processing U is executed. FIG. 13 is a flow chart depicting the cooling water collection processing in FIG. 9.

As FIG. 13 shows, in the cooling water collection processing U, it is determined whether the medical staff operated a cooling water collection button displayed on the operation unit 47 (step U1). If it is determined that the cooling water collection button was not operated, step T6 is repeatedly executed.

Figure 18:
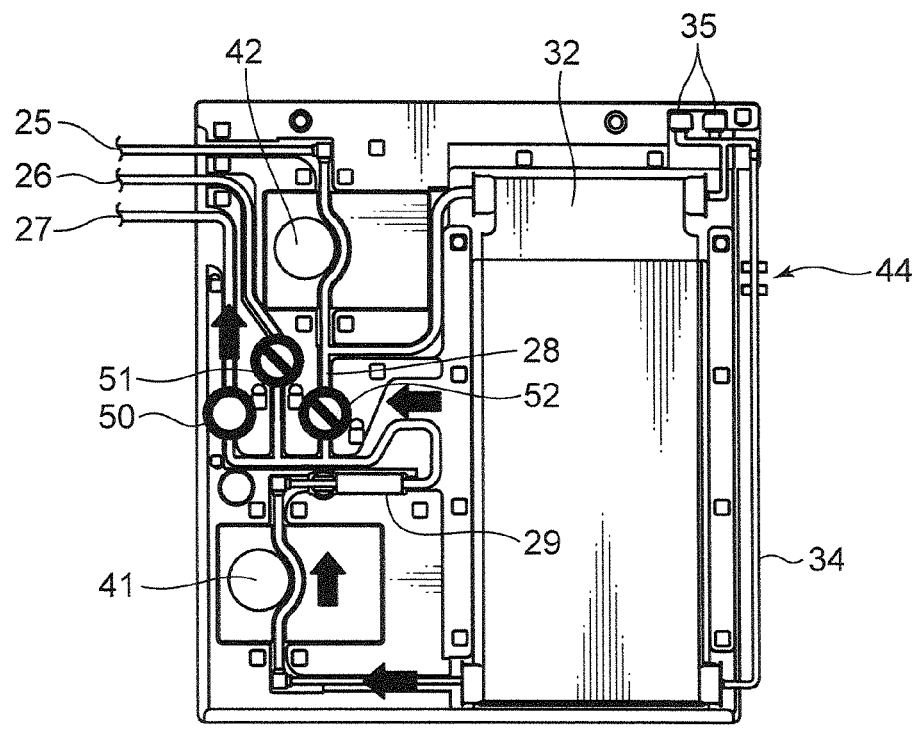
FIG. 18 is a front view depicting a state of collecting the physiological saline in the storage tank in the bag.

If it is determined that the operation button was operated in step U1, the physiological saline solution in the storage tank 32 is collected in step U2. In concrete terms, as FIG. 18 illustrates, the supply tube 26 and the bypass tube 28 are interrupted by the second valve 51 and the third valve 52, and the filling tube 27 is opened by the first valve 50. Further, the first pump 41 is driven in the direction of physiological saline solution being sucked from the storage tank 32. Thereby the physiological saline solution in the storage tank 32 is collected in the bag connected to the filling tube 27 via the supply tube 26 and the filling tube 27.

Then it is determined whether all physiological saline solution in the storage tank 32 is collected (step U3), and if it is determined that all physiological saline solution is not collected, step U2 is repeatedly executed. Whether all physiological saline solution in the storage tank 32 is collected or not can be determined based on the change of the pressure detected by the temperature/pressure sensor 29.

Figure 19:
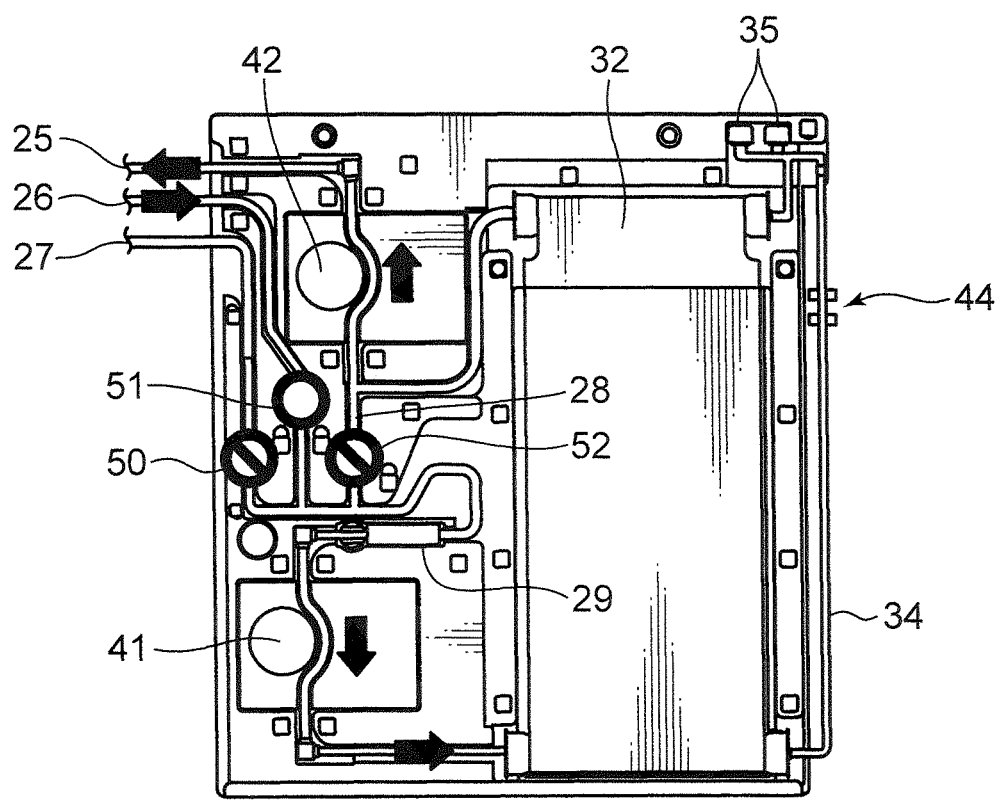
FIG. 19 is a front view depicting a state of collecting the physiological saline solution in the cooling device in the storage tank.

If it is determined that all physiological saline solution in the storage tank 32 is collected in step U3, the remaining physiological saline solution in the brain cooling device 1 is collected in the storage tank 32 in step U4. In concrete terms, as FIG. 19 illustrates, the filling tube 27 and the bypass tube 28 are interrupted by the first valve 50 and the third valve 52, and the supply tube 26 is opened by the second valve 51. In this state, the first pump 41 is driven in the direction of generating the flow toward the storage tank 32, and the second pump 42 is driven in the direction of sucking the fluid from the storage tank 32. Thereby the physiological saline solution in the brain cooling device 1 is collected in the storage tank 32 via the supply tube 26, and the air in the storage tank 32 is guided to the brain cooling device 1 via the collection tube 25.

After step U4 is executed until the predetermined time elapses in step U5, the physiological saline solution in the storage tank 32 is collected in the bag until all physiological saline solution in the storage tank 32 is collected in the same manner as in steps U2 and U3 (steps U6 and U7), and this processing ends.

As described above, according to this embodiment, the rotation speed of the second pump 42 is adjusted so that the pressure in the cuff 4 of the brain cooling device 1 becomes the target pressure. Therefore while maintaining the pressure of the physiological saline solution in the cuff 4 at around the target pressure, the physiological saline can be circulated between the cuff 4 and the storage tank 32.

Furthermore, according to this embodiment, the driving speed of the second pump 42, which drives in the direction of sucking the physiological saline solution from the cuff 4 upon circulating the physiological saline solution, can be adjusted. Hence if the pressure of the physiological saline solution in the cuff 4 becomes unnecessarily high, the pressure can be maintained as mentioned above, while suppressing load applied to the cuff 4 and the wall of the esophagus with which the cuff 4 closely contacts. In concrete terms, if the rotation speed of the first pump 41 is simply lowered in order to decrease the pressure of the physiological saline solution in the cuff 4, the flow rate of the physiological saline solution ejected from the cuff 4 is maintained since the driving speed of the second pump 42 is maintained, hence the pressure of the physiological saline solution in the cuff 4 decreases gradually. In this embodiment, however, at least the driving speed of the second pump 42 can be increased, therefore the pressure of the physiological saline solution in the cuff 4 can be quickly dropped by actively ejecting the fluid in the cuff 4.

In this embodiment, the pressure sensor 10 is disposed on the brain cooling device 1 side. Thereby the distance between the pressure sensor and the cuff 4 can be decreased more than a distance between the pressure sensor and the cuff 4 in the case of disposing the pressure sensor on the brain cooling apparatus 20 side. Since this allows detecting the pressure of the physiological saline solution in the cuff 4 more accurately, the pressure of the physiological saline solution in the cuff 4 can be closer to the target pressure at higher precision if at least the rotation speed of the second pump 42 is adjusted based on this detection result. However the pressure of the physiological saline solution in the cuff 4 can be detected fairly accurately by simply disposing the pressure sensor in a position close to the brain cooling device 1 (e.g. near the ejection side connection unit 25*a* in FIG. 5). Hence the pressure sensor may be disposed on the brain cooling apparatus 20 side.

In this embodiment, the rotation speed of the second pump 42 is controlled based on the pressure detected by the pressure sensor 10. However the rotation speed of the second pump 42 may also be controlled based on the pressure detected by the pressure sensor 7.

In this embodiment, the rotation speed of the second pump 42 is adjusted, while keeping the rotation speed of the first pump 41 constant. Thereby the difference between the rotation speed of the first pump 41 and that of the second pump 42 can be easily adjusted. Since the rotation speed of the first pump 41, which specifies the flow rate of the physiological saline solution to the cuff 4, is constant, the pressure of the physiological saline solution in the cuff 4 can also be maintained approximately at a constant level, while keeping the flow rate of the physiological saline solution to the cuff 4 at a constant level.

Figure 20:
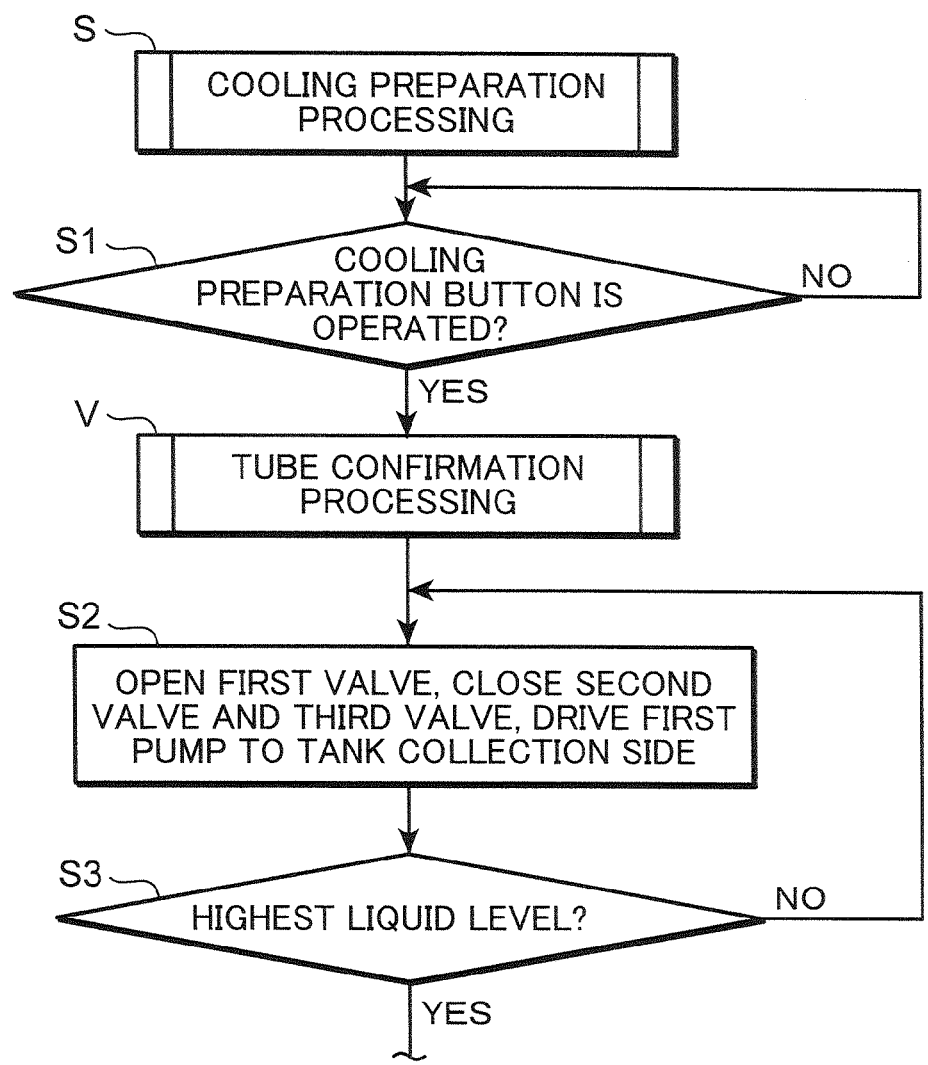
FIG. 20 is a flow chart depicting a processing executed by a control device according to another embodiment of the present invention.
Figure 21:
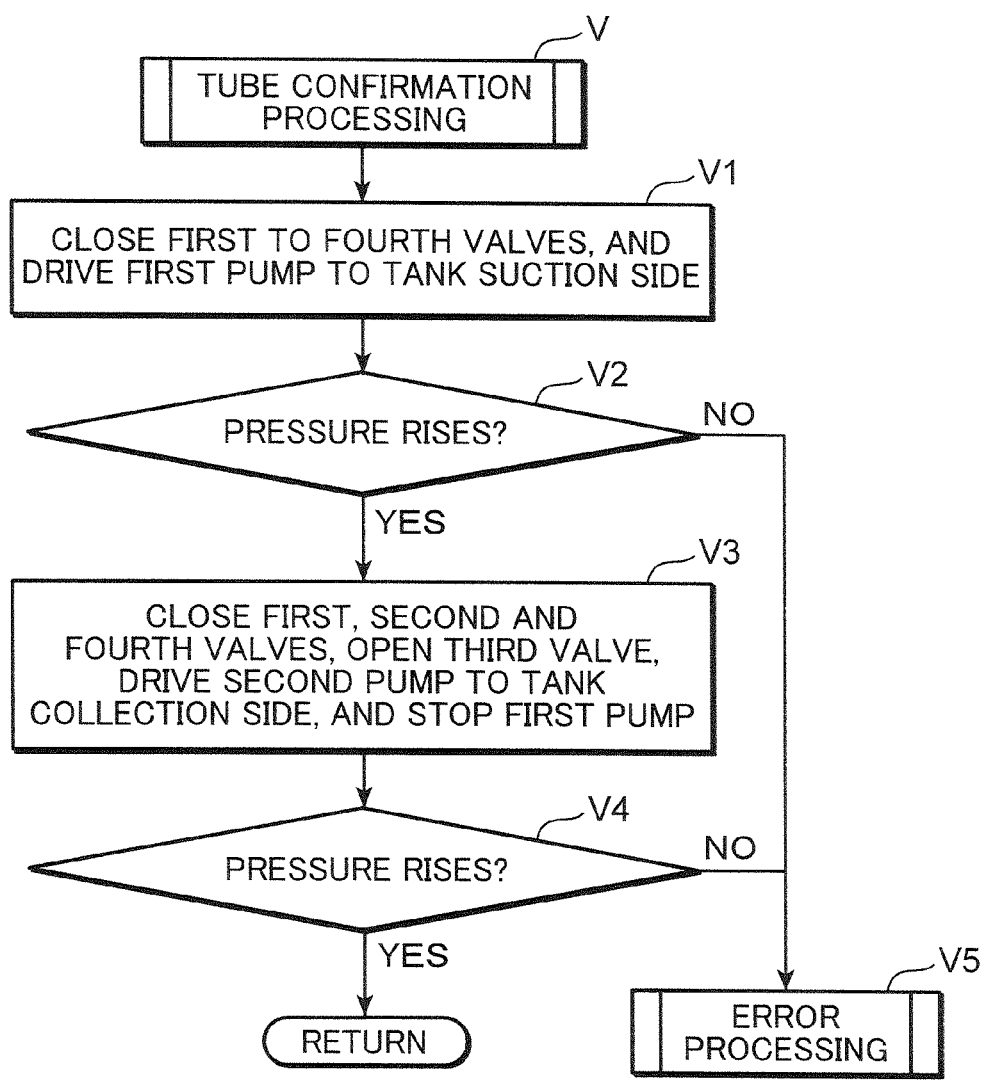
FIG. 21 is a flow chart depicting a processing executed in the tube confirmation processing in FIG. 20.
Figure 22:
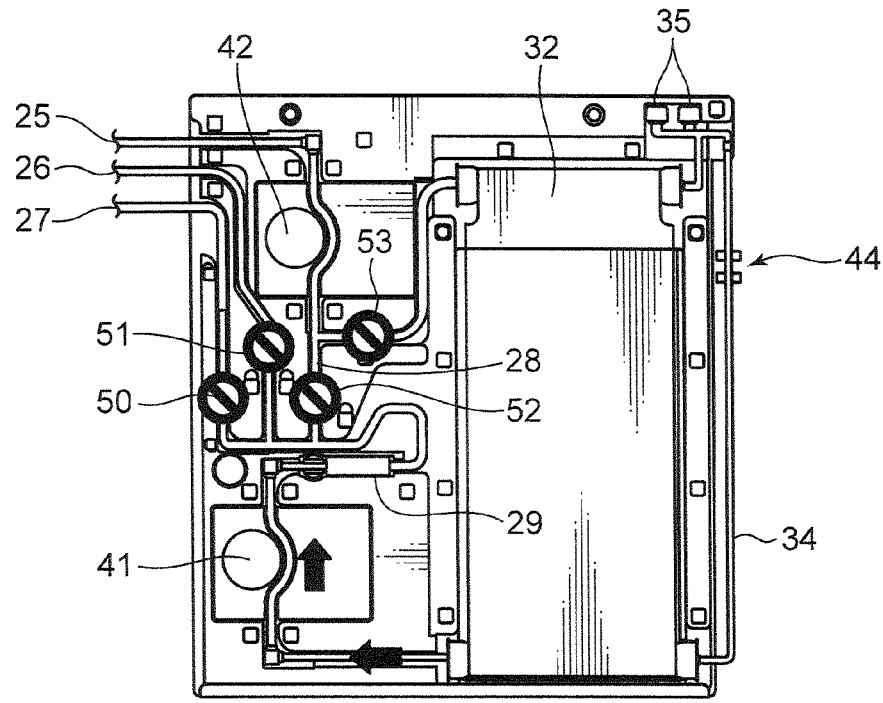
FIG. 22 is a front view depicting an operation of the apparatus main unit according to an embodiment of the present invention, and shows a state of confirming an attached state of the tube to the first pump.
Figure 23:
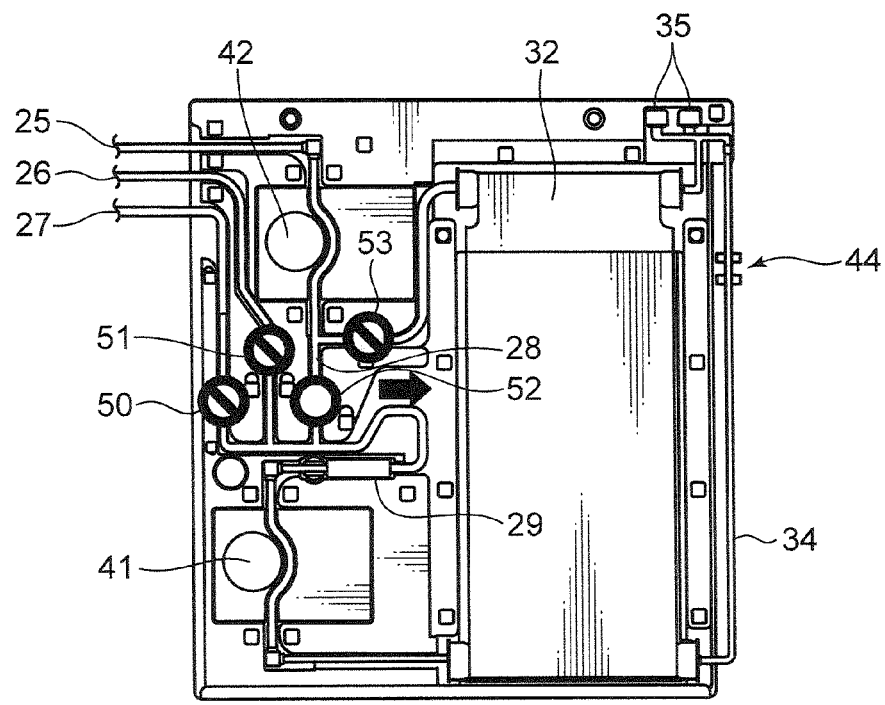
FIG. 23 is a front view depicting an operation of the apparatus main unit according to an embodiment of the present invention, and shows a state of confirming an attached state of the tube to the second pump.

Now another embodiment of the present invention will be described with reference to FIG. 20 to FIG. 23. FIG. 20 is a flow chart depicting a processing executed by a control device according to another embodiment of the present invention. FIG. 21 is a flow chart depicting a processing executed in the tube confirmation processing in FIG. 20. FIG. 22 and FIG. 23 are front views depicting an operation of the apparatus main unit according to an embodiment of the present invention. A composing element the same as the previous embodiment is denoted with a same reference symbol, for which redundant description is omitted.

As FIG. 20 to FIG. 23 show, in this embodiment, the tube confirmation processing V is executed in addition to the above processing executed in this embodiment. In the tube confirmation processing V, it is confirmed whether the supply tube 26 and the collection tube 25 of the channel member 23 are perfectly attached to the first pump 41 and the second pump 42.

In concrete terms, as FIG. 22 illustrates, the apparatus main unit 21 of this embodiment has a fourth valve 53, in addition to the above mentioned first valve 50 to the third valve 52. The fourth valve 53 is for interrupting or opening the collection tube 25 at a portion of the collection tube 25 that is closer to the storage tank 32 than a branch point of the bypass tube 28. Corresponding to the fourth valve 53, a valve hole (not illustrated) for the fourth valve 53, to penetrate through, is provided in the frame member 24. The control device 48 controls driving of the fourth valve 53.

As FIG. 20 shows, if it is determined that the operation button is operated in the cooling preparation processing S (YES in step S1), the tube confirmation processing V is executed. If it is determined that the water level is not the highest level in step S3 (NO in step S3), processing returns to step S2, instead of executing the tube confirmation processing V.

As FIG. 21, if the tube confirmation processing V is executed, the first valve 50 to the fourth valve 53 are closed, as shown in FIG. 22, and the first pump 41 is driven to the tank suction side (step V1). In other words, in step V1, the first pump 41 is driven in a state where the air in the supply tube 26 can go nowhere, whereby the air in the storage tank 32 is sent to the supply tube 26.

Then it is determined whether the pressure detected by the pressure sensor 29 has risen to a predetermined value by driving of the first pump 41 (step V2). In other words, in step V2, it is determined whether a state where the pressure in the supply tube 26 does not rise, even though the first pump 41 is driven, has occurred. In other words, it is determined whether a state where air is not injected into the supply tube 26, because the supply tube 26 is not accurately attached to the first pump 41, has occurred.

If a rise in pressure is not detected in step V2 (NO in step V2), an error processing V5 is performed assuming that the supply tube 26 is not accurately attached to the first pump 41, then processing advances according to the response of the error processing V5. In the error processing V5, the first valve 50 to the fourth valve 53 are opened, and driving the first pump 41 is stopped. Further in the error processing V5, after it is displayed or notified that the supply tube 26 is not accurately attached to the first pump 41 by using the operation unit 47, processing stands by until the medical staff performs the input operation for confirmation.

If a rise in the pressure is detected in step V2 (YES in step V2), operation to confirm whether the collection tube 25 is accurately attached to the second pump 42 is executed in step V3. In concrete terms, in step V3, the first valve 50, the second valve 51 and the fourth valve 53 are closed, as illustrated in FIG. 23, and the third valve 52 is opened. Further in step V3, the second pump 42 is driven toward the collection side after the first pump 41 is stopped. In other words, in step V3, the second pump 42 is driven in a state where the air injected into the supply tube 26 via the collection tube 25 and the bypass tube 28 can go nowhere, whereby the air injected via the collection tube 25 is sent to the supply tube 26.

Then it is determined whether the pressure detected by the pressure sensor 29 has risen to a predetermined value by driving of the second pump 42 (step V4). In other words, in step V4, it is determined whether a state, where the pressure in the supply tube 26 does not rise even thought the second pump 42 is driven, has occurred. In other words, in step V4, it is determined whether a state, where air is not injected into the supply tube 26 because the collection tube 25 is not accurately attached to the second pump 42, has occurred.

If a rise in the pressure is not detected in step V4 (NO in step V4), the error processing V5 is performed assuming that the collection tube 25 is not accurately attached to the second pump 42, then processing advances according to the result of the error processing V5.

If a rise in the pressure is detected in step V4 (YES in step V4), processing returns to the above mentioned step S2, as shown in FIG. 20.

According to this embodiment, it can be confirmed whether the supply tube 26 is perfectly attached to the first pump 41, and whether the collection tube 25 is perfectly attached to the second pump 42. Therefore processing advancing in a state where the attachment of each tube 25 and 26 is incomplete can be prevented.

The above mentioned embodiment primarily includes the invention having the following configurations.

To solve the above mentioned problem, the present invention provides a brain cooling apparatus for supplying a fluid to a containing unit of a brain cooling device and discharging the fluid from the containing unit of the brain cooling device which has the containing unit that can be expanded by the fluid injected therein and closely contact at least a part of an area from an oral cavity to a stomach of a living body, an injection unit that can inject fluid from outside the body into the containing unit, and an ejection unit that can eject the fluid inside the containing unit to outside the body, comprising: an injection side connection unit that can be connected with the injection unit; an ejection side connection unit that can be connected with the ejection unit; a storage unit that stores the fluid; a supply channel that connects the storage unit and the injection side connection unit; a collection channel that connects the storage unit and the ejection side connection unit; a first pump that is disposed on the supply channel to flow the fluid along the supply channel; a second pump that is disposed on the collection channel to flow the fluid along the collection channel; and a control unit that controls driving of the first pump and the second pump, wherein the control unit adjusts a driving speed of at least the second pump out of the two pumps, so that a pressure in the containing unit becomes a preset target pressure in a state of circulating the fluid between the storage unit and the containing unit by driving the first pump such that the fluid flows in a direction from the storage unit to the containing unit, and by driving the second pump such that the fluid flows in a direction from the containing unit to the storage unit.

According to the present invention, the driving speed of at least the second pump is adjusted so that the pressure in the containing unit of the brain cooling device becomes a preset target pressure. Therefore the fluid can be circulated between the containing unit and the storage unit while maintaining the pressure of the fluid inside the containing unit at around the target pressure.

According to the present invention, the driving speed of the second pump, which drives in a direction of sucking the fluid from the containing unit upon circulating the fluid is adjusted. Therefore if the pressure of the fluid inside the containing unit becomes unnecessarily high, the above mentioned pressure can be maintained while suppressing the burden on the containing unit and the wall of the esophagus to which the containing unit closely contacts. In concrete terms, if the driving speed of only the first pump is decreased in order to decrease the pressure of the fluid inside the containing unit, the driving speed of the second pump is maintained, and thereby the flow rate of the fluid ejected from the containing unit is also maintained. As a result, the pressure of the fluid inside the containing unit can be decreased only gradually. Whereas according to the present invention, the driving speed of at least the second pump can be increased. Therefore the pressure of the fluid inside the containing unit can be decreased quickly by actively ejecting the fluid inside the containing unit.

Therefore according to the present invention, the fluid can be circulated between the containing unit and the brain cooling apparatus while appropriately maintaining the pressure of the fluid inside the containing unit of the brain cooling device.

In this brain cooling apparatus, it is preferable that a detection unit that can detect a pressure of the fluid in the brain cooling device is disposed in the brain cooling device, and the control unit adjusts the driving speed of at least the second pump of the two pumps, based on the pressure inside the containing unit detected by the detection unit so that the pressure inside the containing unit becomes the target pressure.

In this aspect, the detection unit is disposed in the brain cooling device. Therefore the position of the detection unit can be closer to the containing unit than that of the detection unit in the case of disposing the detection unit on the brain cooling apparatus side. Hence according to this aspect, the pressure of the fluid inside the containing unit can be detected more accurately, and by adjusting the drive speed of at least the second pump based on this detection result, the pressure of the fluid inside the containing unit can be made close to the target pressure at high accuracy.

In the brain cooling apparatus, it is preferable that the control unit adjusts the driving speed of the first pump to be constant, and adjusts the driving speed of the second pump so that the pressure inside the containing unit becomes the target pressure, in a state of the fluid circulating between the storage unit and the containing unit.

According to this aspect, the drive speed of the first pump is constant. Therefore control for setting the relative speed difference between the first pump and the second pump can be easily performed by adjusting the driving speed of the second pump. The flow rate of the fluid supplied to the containing unit is defined by the driving speed of the first pump. Therefore the above mentioned pressure control, while maintaining the flow rate of the fluid supplied to the containing unit constant, can be performed by adjusting the driving speed of the second pump while maintaining the driving speed of the first pump, as described in this aspect.

It is preferable that the brain cooling apparatus further comprises a cooling unit for cooling the fluid inside the storage unit, and the control unit adjusts a cooling capability of the cooling unit so that a temperature of the fluid inside the storage unit becomes a preset target temperature.

According to this aspect, the fluid inside the storage unit can be cooled by the cooling unit. Hence the fluid can be cooled in the circulation system which circulates the fluid while performing the pressure control as mentioned above, and the brain can be effectively cooled by supplying the fluid cooled like this to the containing unit.

It is preferable that this brain cooling apparatus further comprises a bypass channel that connects an intermediate portion of the supply channel, located in an opposite position from the storage unit with respect to the first pump, and an intermediate portion of the collection channel, located in a position between the second pump and the storage unit, and a valve that can interrupt the supply channel at a position closer to the injection side connection unit than the bypass channel, wherein the second pump interrupts the collection channel when the second pump is in a stop state, and the control unit interrupts the supply channel using the valve, stops the second pump and drives the first pump in a stage before starting circulation of the fluid, to thereby return the fluid inside the storage unit to the storage unit via the collection channel, the bypass channel and the supply channel.

According to this aspect, the fluid inside the storage unit can be circulated (stirred) via the bypass channel by interrupting the supply channel by the valve, and driving the first pump in a state where the collection channel is interrupted by the second pump. As a result, cooling of the fluid by the cooling unit can be sped up.

In the brain cooling apparatus, it is preferable that the fluid is liquid, the supply channel is connected to the storage unit at a position lower than a level of the liquid in the storage unit, and the collection channel is connected to the storage unit at a position higher than the level of the liquid in the storage unit, and in a stage after the circulation of the liquid ends, the control unit drives the second pump in a direction in which the liquid in the collection channel flows toward the containing unit, and drives the first pump in a direction in which the liquid in the supply channel flows toward the storage unit.

According to this aspect, the gas in the storage unit can be guided to the brain cooling device via the supply channel, and fluid inside the cooling device can be guided to the storage unit. Therefore the liquid inside the cooling device can be collected in the storage unit after the cooling device is used.

The present invention also provides a brain cooling device that is used by being connected to the above mentioned brain cooling apparatus, comprising: a containing unit that can be expanded by the fluid injected therein and closely contact at least a part of an area from an oral cavity to a stomach of a living body, in a state of being inserted orally or transnasally into the living body; an injection unit that can inject fluid from outside the body into the containing unit and can be connected to the injection side connection unit of the brain cooling apparatus; an ejection unit that can eject the fluid inside the containing unit to outside the body, and can be connected to the ejection side connection unit of the brain cooling apparatus; and a detection unit that can detect a pressure of the fluid inside the injection unit or the ejection unit, and can output the detection result to the control unit of the brain cooling apparatus.

According to the brain cooling device of the present invention, the injection unit and the ejection unit can be connected to the injection side connection unit and the ejection side connection unit respectively, and the detection result by the detection unit can be output to the control unit of the brain cooling apparatus. Therefore the brain cooling device of the present invention can be suitably used for the brain cooling apparatus which can maintain an appropriate pressure of the fluid in the containing unit.

INDUSTRIAL APPLICABILITY

The present invention can provide a brain cooling apparatus that can circulate a fluid between the containing unit of the brain cooling device and the brain cooling apparatus while maintaining an appropriate pressure of the fluid in the containing unit, and a brain cooling device suitable thereto.

The invention claimed is:

1. A brain cooling apparatus adapted for a brain cooling device, the brain cooling device having a containing unit that can be expanded by the fluid injected therein and closely contact at least a part of an area from an oral cavity to a stomach of a living body, an injection unit that can inject fluid from outside the body into the containing unit, and an ejection unit that can eject the fluid inside the containing unit to outside the body, the brain cooling apparatus comprising:
   an injection side connection unit that can be connected with the injection unit;
   an ejection side connection unit that can be connected with the ejection unit;
   a storage unit that stores the fluid;
   a supply channel that connects the storage unit and the injection side connection unit;
   a collection channel that connects the storage unit and the ejection side connection unit;
   a first pump that is disposed on the supply channel to cause the fluid to flow along the supply channel;
   a second pump that is disposed on the collection channel to cause the fluid to flow along the collection channel; and
   a control unit that controls driving of the first pump and the second pump, wherein
   the control unit adjusts a driving speed of at least the second pump, so that a pressure in the supply channel or the collection channel becomes a preset target pressure in a state of driving the first pump such that the fluid flows in a direction from the storage unit to the injection side connection unit and driving the second pump such that the fluid flows in a direction from the ejection side connection unit to the storage unit, and
   the control unit increases the driving speed of the second pump when the pressure in the supply channel or the collection channel is higher than the target pressure.

2. The brain cooling apparatus according to claim 1, further comprising:
   a pressure sensor capable of detecting a pressure of the fluid in the supply channel or the collection channel, wherein
   the control unit increases the driving speed of the second pump when the pressure in the supply channel or the collection channel detected by the pressure sensor is higher than the target pressure, so that the pressure inside the supply channel or the collection channel becomes the target pressure.

3. The brain cooling apparatus according to claim 1, wherein
   the control unit adjusts the driving speed of the first pump to be constant, and increases the driving speed of the second pump when the pressure in the supply channel or the collection channel is higher than the target pressure, so that the pressure inside the supply channel or the collection channel becomes the target pressure, in a state of driving the first pump such that the fluid flows in a direction from the storage unit to the injection side connection unit and driving the second pump such that the fluid flows in a direction from the ejection side connection unit to the storage unit.

4. The brain cooling apparatus according to claim 1, further comprising a cooling unit for cooling the fluid inside the storage unit, wherein
   the control unit adjusts a cooling capability of the cooling unit so that a temperature of the fluid inside the storage unit becomes a preset target temperature.

5. The brain cooling apparatus according to claim 4, further comprising:
   a bypass channel that connects an intermediate portion of the supply channel, located in an opposite position from the storage unit with respect to the first pump, and an intermediate portion of the collection channel, located in a position between the second pump and the storage unit; and
   a valve that can interrupt the supply channel at a position closer to the injection side connection unit than the bypass channel, wherein
   the second pump interrupts the collection channel when the second pump is in a stop state, and
   the control unit interrupts the supply channel using the valve, stops the second pump and drives the first pump, to thereby return the fluid inside the storage unit to the storage unit via the collection channel, the bypass channel and the supply channel.

6. The brain cooling apparatus according to claim 1, wherein
   the fluid is liquid,
   the supply channel is connected to the storage unit at a position lower than a level of the liquid in the storage unit, and the collection channel is connected to the storage unit at a position higher than the level of the liquid in the storage unit, and
   the control unit drives the second pump in a direction in which the liquid in the collection channel flows toward the ejection side connection unit, and drives the first pump in a direction in which the liquid in the supply channel flows toward the storage unit.

7. A system comprising a brain cooling device and a brain cooling apparatus connected to the brain cooling device, wherein
   the cooling device includes:
      a containing unit that can be expanded by the fluid injected therein and closely contact at least a part of an area from an oral cavity to a stomach of a living body;
      an injection unit that can inject fluid from outside the body into the containing unit; and
      an ejection unit that can eject the fluid inside the containing unit to outside the body;
   the cooling apparatus includes:
      an injection side connection unit connected with the injection unit;
      an ejection side connection unit connected with the ejection unit;
      a storage unit storing the fluid;
      a supply channel connecting the storage unit and the injection side connection unit;
      a collection channel connecting the storage unit and the ejection side connection unit;
      a first pump disposed on the supply channel to cause the fluid to flow along the supply channel;
      a second pump disposed on the collection channel to cause the fluid to flow along the collection channel;
      a control unit that controls driving of the first pump and the second pump;
   the control unit adjusts a driving speed of at least the second pump out of the two pumps, so that a pressure in the containing unit becomes a preset target pressure in a state of circulating the fluid between the storage unit and the containing unit by driving the first pump such that the fluid flows in a direction from the storage unit to the containing unit, and by driving the second pump such that the fluid flows in a direction form the containing unit to the storage unit, and the control unit increases the driving speed of the second pump when the pressure in the containing unit is higher than the target pressure.

8. The system according to claim 7, wherein
the brain cooling device includes a detection unit that can detect a pressure of the fluid in the containing unit, and
the control unit increases the driving speed of the second pump when the pressure inside the containing unit detected by the detection unit is higher than the target pressure, so that the pressure inside the containing unit becomes the target pressure.

9. The system according to claim 7, wherein the control unit adjusts the driving speed of the first pump to be constant, and increases the driving speed of the second pump when the pressure inside the containing unit is higher than the target pressure, so that the pressure inside the containing unit becomes the target pressure, in a state of the fluid circulating between the storage unit and the containing unit.

10. The system according to claim 7, wherein
the brain cooling apparatus includes a cooling unit for cooling the fluid inside the storage unit, and
the control unit adjusts a cooling capability of the cooling unit so that a temperature of the fluid inside the storage unit becomes a preset target temperature.

11. The system according to claim 10, wherein
the brain cooling apparatus includes:
a bypass channel that connects an intermediate portion of the supply channel, located in an opposite position from the storage unit with respect to the first pump, and an intermediate portion of the collection channel, located in a position between the second pump and the storage unit; and
a valve that can interrupt the supply channel at a position closer to the injection side connection unit than the bypass channel;
the second pump interrupts the collection channel when the second pump is in a stop state; and
the control unit interrupts the supply channel using the valve, stops the second pump and drives the first pump in a stage before starting circulation of the fluid, to thereby return the fluid inside the storage unit to the storage unit via the collection channel, the bypass channel and the supply channel.

12. The system according to claim 7, wherein
the fluid is liquid,
the supply channel is connected to the storage unit at a position lower than a level of the liquid in the storage unit, and the collection channel is connected to the storage unit at a position higher than the level of the liquid in the storage unit, and
in a stage after the circulation of the liquid ends, the control unit drives the second pump in a direction in which the liquid in the collection channel flows toward the containing unit, and drives the first pump in a direction in which the liquid in the supply channel flows toward the storage unit.

\* \* \* \* \*